United States Patent [19]
Goto et al.

[11] Patent Number: 5,620,973
[45] Date of Patent: Apr. 15, 1997

[54] TETRACYCLIC CONDENSED HETEROCYCLIC COMPOUNDS AND THEIR USE

[75] Inventors: Giichi Goto, Osaka; Yuji Ishihara; Masaomi Miyamoto, both of Hyogo, all of Japan

[73] Assignee: Takeda Chemical Industries, Ltd., Osaka, Japan

[21] Appl. No.: 330,133

[22] Filed: Oct. 25, 1994

[30] Foreign Application Priority Data

Nov. 30, 1993 [JP] Japan ................................. 5-299799
Mar. 25, 1994 [JP] Japan ................................. 6-055984

[51] Int. Cl.$^6$ .................. C07D 487/04; A61K 31/55
[52] U.S. Cl. .................. 514/214; 540/576; 544/372; 546/71; 546/72; 546/200
[58] Field of Search .................. 540/576; 514/214

[56] References Cited

U.S. PATENT DOCUMENTS

| | | | |
|---|---|---|---|
| 3,403,156 | 9/1968 | Humber et al. | 260/286 |
| 4,192,874 | 3/1980 | Glamkowski et al. | 424/248.54 |
| 5,273,974 | 12/1993 | Goto et al. | 514/221 |

FOREIGN PATENT DOCUMENTS

| | | |
|---|---|---|
| 378207 | 7/1990 | European Pat. Off. |
| 441517 | 8/1991 | European Pat. Off. |
| 457908 | 11/1991 | European Pat. Off. |
| 560235 | 9/1993 | European Pat. Off. |
| 562832 | 9/1993 | European Pat. Off. |
| 0607864 | 7/1994 | European Pat. Off. |
| 93/07140 | 4/1993 | WIPO. |
| 93/12085 | 6/1993 | WIPO. |

OTHER PUBLICATIONS

Kumar et al., *Treatment of Alzheimer's disease with cholinergic drugs*, International Journal of Clinical Pharmacology, Therapy and Toxicology, vol. 29, No. 1, 1991, pp. 23–37.
Ogino et al., *Photocycloadditions of p–Quinones to Ketenimines*, J. C. S. Perkin I, 1979, pp. 1552–1559.
Ishihara et al., *Synthesis of Isoindolo[2,1–a]–quinoline Derivatives* . . . , Chem Pharm Bull., vol. 38, No. 11, 1990, pp. 3024–3030.
Rehacek et al., Ergot Alkaloids, *Bioactive Molecules*, vol. 12, 1990, pp. 68–76.
Walker et al., *Novel Syntheses of 1,4–Benzodiazepines, Isoindolo[2,1–d][1,4]benzodiazepines*, . . . , Journal of Organic Chemistry, vol. 37, No. 24, 1972, pp. 3755–3770.
Pecca et al., *Synthetic Trypanocides.*, Journal of Medicinal Chemistry, vol. 14, No. 5, 1971 pp. 448–449.
Itoh et al., *Synthesis and Angiotensin Converting Enzyme–Inhibitory Activity* . . . , Chem. Pharm. Bull., vol. 34, No. 9, 1986, pp. 3747–3761.
Blicke, *The Mannich Reaction*, Organic Reactions vol. 1, Chapter 10, pp. 303–341, (1942).
J.D. Sweatt et al., Archives Internationales de Phartmacodynamie et de Therapie, 1982, 257:188–199.
M. Leboeuf et al., Annales Pharmaceutiques Francaises, 1980, 38(6):537–544.
J.D. Sweatt et al., Archives Internationales de Pharmacodynamie et de Therapie, 1982, 257:188–199.
M. Hirobe et al., Chemical Abstracts, Abstract 181036j, 1980, 92(21):641.
G.N. Artemenko et al, Chemical Abstracts, Abstract 69985g, 1972, 77(11):11.
L.A. Aksanova et al., Chemical Abstracts, Abstract 34140e, 1972, 76(7):310.
N.J. Doorenbos et al., Journal of Pharmaceutical Sciences, 1971, 60(8):1236–1238.
N.M. Sharkova et al., Chemical Abstracts, Abstract 115036d, 1969, 70(25):335.

*Primary Examiner*—Philip I. Datlow
*Attorney, Agent, or Firm*—Foley & Lardner

[57] ABSTRACT

A novel compound of the formula

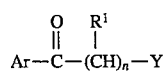

wherein Ar represents a tetracyclic fused heterocyclic group which may be substituted; $R^1$ represents H or a hydrocarbon group which may be substituted; Y represents an amino or nitrogen-containing saturated heterocyclic group which may be substituted, its salt, inhibiting excellent cholinesterase inhibitory activity and monoamine uptake inhibitory activity, thus being useful as therapeutic and/or prophylactic medicaments of senile dementia.

10 Claims, No Drawings

TETRACYCLIC CONDENSED HETEROCYCLIC COMPOUNDS AND THEIR USE

This invention relates to a medicine and more particularly to a cholinesterase inhibitor composition, inter alia a therapeutic and/or prophylactic drug for senile dementia and symptoms of senile dementia in Altzheimer's and other diseases, a novel tetracyclic fused heterocyclic derivative or a salt thereof for use as its active ingredient, and processes for its production.

With an increasing mean age of the population, a variety of compounds having therapeutic and/or prophylactic effects on senile dementia have so far been proposed. Among them, tacrine (THA) and physostigmine, both of which are inhibitors of cholinesterase, have been found to have anti-senile dementia activity [cf. International Journal of Clinical Pharmacology, Therapy and Toxicology, Vol. 29, No. 1, p. 23–37, 1991, etc.]. However, severe hepatic impairment is often associated with THA, while physostigmine has the drawback of a short duration of action and a high toxic potential.

Meanwhile, naturally-occurring ergot alkaloids are known to be tetracyclic fused heterocyclic compounds having an (iso)indole ring. Particularly as to dihydroergotoxine and nicergoline, their potential utility as therapeutic agents for senile dementia has been explored (Z. REHACEK and P. SAJDL., "Bioactive Molecules. vol. 12: ERGOT ALKALOIDS", ELSVIER, 1990, p. 74).

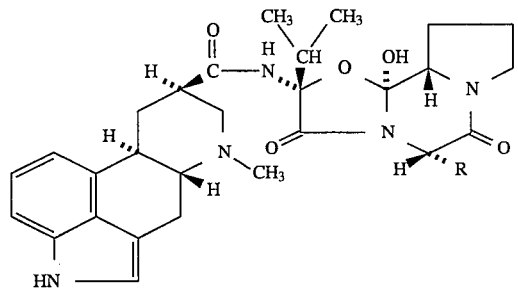

Dihydroergotoxine

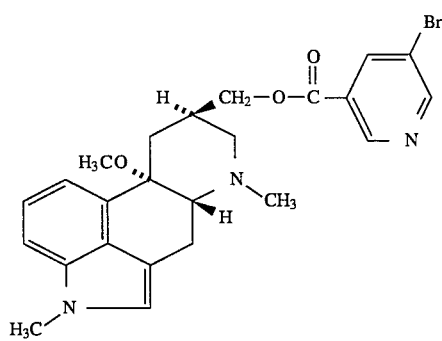

Nicergoline

However, there is no disclosure, nor a suggestion, in the literature about cholinesterase inhibitory activity in these compounds.

Meanwhile, as synthetic versions, a variety of bicyclic or tricyclic fused heterocyclic compounds each having a (dihydro)indole ring have been proposed as inhibitors of cholinesterase (JP-A-4(1992)-234845, JP-A-5(1993)-140149, W09307140 and 9312085, and EP560235 and 562832).

JP-A-4(1992)-234845 discloses a tricyclic cyclicamine compound of the formula

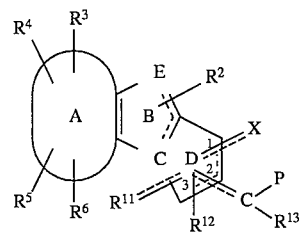

[wherein P represents an N-substituted piperidin-1-yl (N-substituted piperazin-1-yl)methyl group or the like; G represents carbon or nitrogen; E represents carbon, nitrogen, oxygen or sulfur; ring A represents an aromatic ring such as benzene, pyridine, thiophene or the like] and a pharmaceutical composition comprising the same compound as an active ingredient.

It is described there that compounds of formula [I] having the above ABD ring system, which includes such species as 1H-pyrrolo[1,2-a]indol-1-one, cyclopento[d]indol-3-one, cyclopento[b](benzo[b]thieno)-1-one, 1H-pyrrolo[1,2-a](6-azaindol)-1-one, pyrrolo[1,2-a](thieno[2,3-b]pyrrol)-1-one, etc., have cholinesterase inhibitory activity and a pharmaceutical composition comprising any of the compounds as an active ingredient is instrumental for augmentation of memory in patients with dementia or Altzheimer's disease. Specifically, the following compound has been described, among others.

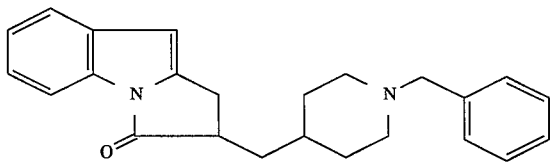

JP-A5(1993)-140149 discloses a fused heterocyclic derivative of the formula

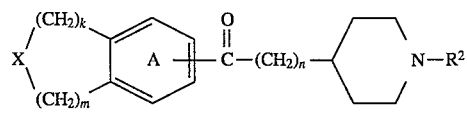

wherein X represents $R^1$—N< ($R^1$ represents a hydrogen atom, a hydrocarbon group which may be substituted or an acyl group which may be substituted), an oxygen atom or a sulfur atom; $R^2$ represents a hydrogen atom or a hydrocarbon group which may be substituted; ring A represents a benzene ring which may be substituted; k represents a whole number of 0–3; m represents a whole number of 1–8; n represents a whole number of 1–6, or a salt thereof. Specifically, the following compound, among others, has been disclosed.

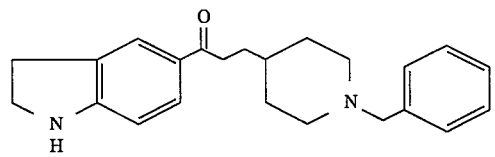

WO9307140 discloses a compound of the formula

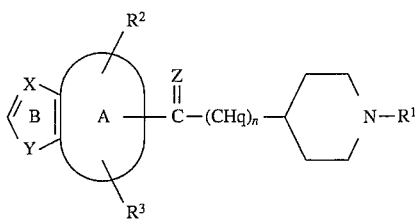

[wherein ring A represents benzo, thieno, pyrido, pyrazino, pyrimido, furano, seleno, pyrrolo, thiazolo or imidazolo; $R^1$ represents phenyl, phenyl($C_1$–$C_6$)alkyl, cinnamyl or heteroarylmethyl (where the heteroaryl represents imidazolo, thiazolo, thieno, pyrido or isoxazolo); said phenyl and heteroaryl each may have 1–2 substituent groups selected from among ($C_1$–$C_6$)alkyl, ($C_1$–$C_6$)alkoxy and halogen; $R^2$ and $R^3$ each represents hydrogen, ($C_1$–$C_6$)alkoxy or ($C_1$–$C_6$)alkyl [where the alkyl may be substituted by 1–3 substituent groups selected from fluoro, benzyloxy, hydroxy, phenyl, benzyl, halogen, nitro, cyano, $CO_2R^4$, $CONHR^4$, $NR^4R^5$, $NR^4COR^5$ and $SO_pCH_2Ph$ (where p is equal to 0, 1 or 2) or $R^2$ and $R^3$ may, taken together with the adjacent carbon atom, represent a 5- or 6-membered ring (the ring constituent atoms are selected from among carbon, nitrogen and oxygen; e.g. methylenedioxy, ethylenedioxy, or a lactam ring); $R^4$ and $R^5$ independently represent a hydrogen atom or a ($C_1$–$C_6$)alkyl group; $R^4$ and $R^5$ of said $NR^4R^5$ may, taken together with the adjacent nitrogen atom, form a 4- through 8-membered ring containing at least one nitrogen atom (the other ring constituent atoms are selected from carbon, oxygen and nitrogen); $R^4$ and $R^5$ of said $NR^4COR^5$ may, taken together with the adjacent nitrogen and carbon atoms, form a 4- through 8-membered lactam ring; X represents nitrogen or CH; Y represents oxygen, sulfur or $NR^6$; $R^6$ represents hydrogen, ($C_1$–$C_6$)alkyl, $CO(C_1$–$C_6$)alkyl or $SO_2$-phenyl [the phenyl may have 1–5 substituent groups independently selected from ($C_1$–$C_4$)alkyl groups; n represents a whole number of 1 through 4; q in each occurrence independently represents 1 or 2; Z represents oxygen or sulfur]. Specifically, the following compound, among others, has been disclosed.

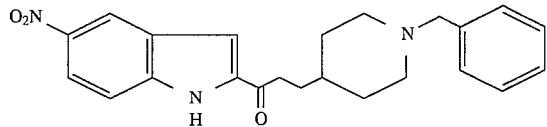

WO9312085 discloses a compound of the formula

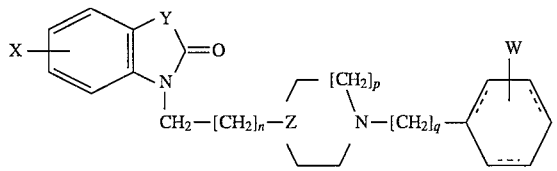

wherein X represents 1 or more substituent groups independently selected from hydrogen, lower alkyl, aryl, aryloxy, cyano, lower alkoxy, halogen, hydroxy, nitro, trifluoromethyl, alkylsulfonamido, NHCOR (where R represents lower alkyl or aryl), $NR_1R_2$ (where $R_1$ and $R_2$ independently represents a hydrogen atom or a lower alkyl group or combindly form a ring), and $CO_2R$ (where R represents lower alkyl, cycloalkyl, cycloalkenyl or bicycloalkyl, which may be further substituted by lower alkyl); Y represents CO or $CR_3R_4$ ($R_3$ and $R_4$ independently represents hydrogen, lower alkyl or lower alkoxy or jointly form a cycloacetal group); Z represents nitrogen or CH. Specifically, the following compound, among others, has been described.

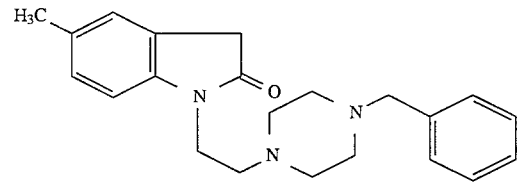

EP560235 discloses a fused heterocyclic ketone derivative of the formula

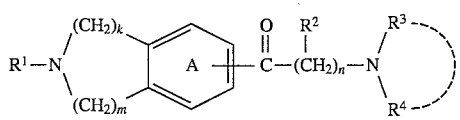

wherein $R^1$ represents a hydrogen atom, a hydrocarbon group which may be substituted or an acyl group which may be substituted; ring A represents a benzene ring which may be substituted; n represents a whole number of 1 through 10; $R^2$, $R^3$ and $R^4$ are the same or different and each represents a hydrogen atom or a hydrocarbon group which may be substituted; or $R^3$ and $R^4$ may, taken together with the adjacent nitrogen atom, form a heterocyclic group; $R^2$ may be different with different repeats of n; k represents a whole number of 0 through 3; m represents a whole number of 1 through 8; provided, however, that where k=0 and m=2, n>1, or a salt thereof. Specifically, the following compound, among others, has been disclosed.

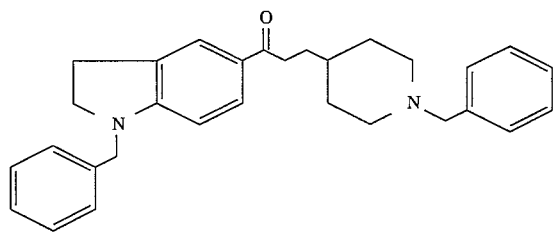

EP562832 discloses a compound of the formula

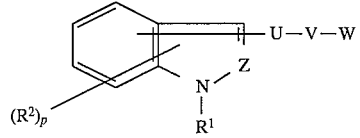

wherein $R^1$ and $R^2$ each represents a hydrogen atom or an organic group; p represents 0, 1, 2 or 3; U represents —CO— or —CH(OR$^3$)— (where $R^3$ represents a hydrogen atom or a hydroxy-protecting group); V represents an aliphatic hydrocarbon group which may be unsaturated; W represents a nitrogen-containing group. Specifically, the following compound, among others, has been described.

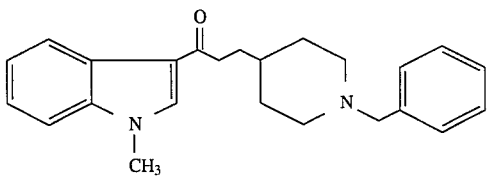

However, none of these official papers mention or even suggest a tetracyclic fused heterocyclic group.

In the face of an increasing incidence of senile dementia, there is a strong demand for an anti-senile dementia agent which is longer in the duration of action and lower in the toxicological risk level than the hitherto-known compounds having therapeutic or prophylactic effects on senile dementia.

Under the circumstances, the inventors of this invention explored into the biological and pharmacological activities of various heterocyclic compounds including novel compounds and found surprisingly that a novel class of compounds having a unique chemical structure representing a direct combination between a tetracyclic fused heterocycle and a group of the formula

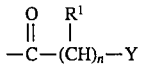

wherein the symbols have the same meanings as defined below] has excellent cholinesterase inhibitory activity and monoamine reuptake inhibitory activity on account of said unique chemical structure and is, therefore, of value as a therapeutic and/or prophylactic agent for senile dementia. They have accordingly brought this invention into being.

Thus, this invention relates to:

(1) a compound of the formula

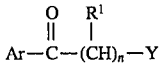 (I)

wherein Ar represents a tetracyclic fused heterocyclic group which may be substituted; n represents a whole number of 1 through 10; $R^1$ represents a hydrogen atom or a hydrocarbon group which may be substituted and may be different from one another in the repitition of n; Y represents an unsubstituted or substituted amino or nitrogen-containing saturated heterocyclic group which may be substituted, or a salt thereof;

(2) A process for producing the compound (I) which comprises reacting a compound of the formula

 (II)

wherein Ar has the same meaning as defined above, or a salt thereof with a compound of the formula

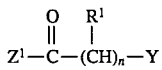 (III)

wherein $R^1$, Y and n have the same meanings as defined above; $Z^1$ represents a leaving group, or a salt thereof.

(3) A process for producing a compound of the formula

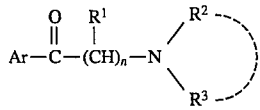 (VI)

wherein $R^2$ and $R^3$ each represents a hydrogen atom, a hydrocarbon group which may be substituted or an acyl group which may substituted; $R^2$ and $R^3$ may, taken together with the adjacent nitrogen atom, jointly form a nitrogen-containing saturated heterocyclic group which may be substituted; the other symbols have the same meanings as defined above, or a salt thereof which comprises reacting a compound of the formula

 (IV)

or a salt thereof with a compound of the formula

 (V)

or a salt thereof wherein $Z^2$ and $Z^3$ represent groups which react with each other and leave together; the other symbols have the same meanings as above.

(4) A cholinesterase inhibitor composition comprising the compound (I).

(5) A therapeutic and/or prophylactic agent for senile dementia which contains the compound (I).

The compound (I) or its salt, of this invention is a novel compound having a characteristic chemical structure comprising a tetracyclic fused heterocycle substituted by a substituent group of the formula

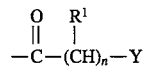

and, because of this characteristic structure, exhibits potent anti-senile dementia activity.

Referring to the above formula, n represents a whole number of 1 through 10.

Referring, further, to the formula, $R^1$ represents a hydrogen atom or a hydrocarbon group which may be substituted and may be different from one another in the repetition of n.

The "hydrocarbon group" of said "hydrocarbon group which may be substituted", as represented by $R^1$, includes $C_{1-18}$ hydrocarbon groups which may be either chain or cyclic or mixed chain and cyclic. Among such chain hydrocarbon groups are straight-chain or branched $C_{1-11}$ alkyl (e.g. methyl, ethyl, n-propyl, i-propyl, n-butyl, i-butyl, tert-butyl, n-pentyl, n-hexyl, etc.), straight-chain or branched $C_{2-6}$ alkenyl (e.g. vinyl, allyl, 2-butenyl, etc.), and straight-chain or branched $C_{2-6}$ alkynyl (e.g. propargyl, 2-butynyl, etc.), among others. Among said cyclic hydrocarbon groups are $C_{3-7}$ monocyclic cycloalkyl (e.g. cyclobutyl, cyclopentyl, cyclohexyl, etc.), $C_{8-14}$ bridged ring saturated hydrocarbon groups (e.g. bicyclo[3.2.1]oct-2-yl, bicyclo[3.3.1]non-2-yl, adamantan-1-yl, etc.), $C_{6-14}$ aryl (e.g. phenyl, naphthyl, etc.) and so on.

Among said mixed chain and cyclic type hydrocarbon groups are $C_{7-18}$ aralkyl (e.g. phenyl-$C_{1-12}$ alkyl or naphthyl-$C_{1-8}$ alkyl, such as benzyl, phenylethyl, phenylpropyl, phenylbutyl, phenylpentyl, phenylhexyl, α-naphthylmethyl, etc., diphenyl-$C_{1-3}$ alkyl such as diphenylmethyl, diphenylethyl, etc.), $C_{6-14}$ aryl-$C_{2-12}$ alkenyl (e.g. phenyl-$C_{2-12}$ alkenyl such as styryl, cinnamyl, 4-phenyl-2-butenyl, 4-phenyl-3-butenyl, etc.), $C_{6-14}$ aryl-$C_{2-12}$ alkynyl (e.g. phenyl-$C_{2-12}$ alkinyl such as phenylethinyl, 3-phenyl-2-propinyl, 3-phenyl-1-propinyl, etc.), $C_{3-7}$ cycloalkyl-$C_{1-6}$ alkyl (e.g. cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, cycloheptylhexyl, etc.) and so on.

The "hydrocarbon group" for $R^1$ is preferably a straight-chain or branched $C_{1-11}$ alkyl group, more preferably a straight-chain or branched $C_{1-7}$ alkyl group (e.g. methyl, ethyl, n-propyl i-propyl, n-butyl, i-butyl, tert-butyl, n-pentyl, n-hexyl, etc.), or a $C_{7-8}$ aralkyl group, more preferably a $C_{7-10}$ aralkyl group (e.g. phenyl($C_{1-4}$)alkyl such as benzyl, phenylethyl, phenylpropyl, etc.).

The 'hydrocarbon group', represented by $R^1$, may be substituted by various groups including those which are commonly used as substituents for hydrocarbon groups. Specifically, the above-described $C_{1-11}$ alkyl, $C_{2-6}$ alkenyl, $C_{2-6}$ alkynyl, $C_{3-7}$ monocyclic cycloalkyl or $C_{8-14}$ bridged ring saturated hydrocarbon group may have 1 to 5 substituents selected from halogen (e.g. fluoro, chloro, bromo, iodo), nitro, cyano, hydroxy, $C_{1-4}$ alkoxy (e.g. methoxy, ethoxy, propyloxy, butyloxy, isopropyloxy, etc.), $C_{1-4}$ alkylthio (e.g. methylthio, ethylthio, propylthio, etc.), amino, mono- or di-$C_{1-4}$ alkylamino (e.g. methylamino, ethylamino, propylamino, dimethylamino, diethylamino, etc.), 5- through 7-membered cycloamino groups which may have 1–3 hetero-atoms selected from among N, O and S in addition to the amino nitrogen atom (e.g. pyrrolidino, piperidino, morpholino, etc.), $C_{1-4}$ alkyl-carbonylamino (e.g. acetylamino, propionylamino, butyrylamino, etc.), $C_{1-4}$ alkylsulfonylamino (e.g. methylsulfonylamino, ethylsulfonylamino, etc.), $C_{1-4}$ alkoxy-carbonyl (e.g. methoxycarbonyl, ethoxycarbonyl, propoxycarbonyl, etc.), carboxyl, $C_{1-6}$ alkyl-carbonyl (e.g. methylcarbonyl, ethylcarbonyl, propylcarbonyl, etc.), carbamoyl, mono- or di-$C_{1-4}$ alkyl-carbamoyl (e.g. methylcarbamoyl, ethylcarbamoyl etc.), $C_1$-$C_6$ alkylsulfonyl (e.g. methylsulfonyl, ethylsulfonyl, propylsulfonyl, etc.) and so on.

The substituents by which the $C_{6-14}$ aryl, $C_{7-18}$ aralkyl, $C_{6-14}$ aryl-$C_{2-12}$ alkenyl, $C_{6-14}$ aryl-$C_{2-12}$ alkinyl or $C_{3-7}$ cycloalkyl-$C_{1-6}$ alkyl for $R^1$ may be substituted are $C_{1-4}$ alkyl (e.g. methyl, ethyl, propyl, butyl, etc.), halogen (e.g. fluoro, chloro, bromo, iodo), nitro, cyano, hydroxy, $C_{1-4}$ alkoxy (e.g. methoxy, ethoxy, propyloxy, butyloxy, isopropyloxy, etc.), $C_{1-4}$ alkylthio (e.g. methylthio, ethylthio, propylthio, isopropylthio, butylthio, etc.), amino, mono- or di-$C_{1-4}$ alkylamino (e.g. methylamino, ethylamino, propylamino, dimethylamino, diethylamino, etc.), 5- through 7-cycloamino which may have 1–3 hetero-atoms selected from among N, O and S in addition to the amino nitrogen atom (e.g. pyrrolidino, piperidino, morpholino, etc.), $C_{1-4}$ alkyl-carbonylamino (e.g. acetylamino, propionylamino, butyrylamino, etc.), aminocarbonyloxy, mono- or di-$C_{1-4}$ alkylaminocarbonyloxy (e.g. methylaminocarbonyloxy, ethylaminocarbonyloxy, dimethylaminocarbonyloxy, diethylaminocarbonyloxy, etc.), $C_{1-4}$ alkylsulfonylamino (e.g. methylsulfonylamino, ethylsulfonylamino, propylsulfonylamino, etc.), $C_{1-4}$ alkoxy-carbonyl (e.g. methoxycarbonyl, ethoxycarbonyl, propoxycarbonyl, isobutoxycarbonyl, etc.), carboxyl, $C_{1-6}$ alkyl-carbonyl (e.g. methylcarbonyl, ethylcarbonyl, butylcarbonyl, etc.), $C_{3-7}$ cycloalkyl-carbonyl (e.g. cyclohexylcarbonyl etc.), carbamoyl, mono- or di-$C_{1-4}$ alkyl-carbamoyl (e.g. methylcarbamoyl, ethylcarbamoyl, propylcarbamoyl, butylcarbamoyl, diethylcarbamoyl, dibutylcarbamoyl, etc.), $C_{1-6}$ alkylsulfonyl (e.g. methylsulfonyl, ethylsulfonyl, propylsulfonyl, etc.), $C_{3-7}$ cycloalkylsulfonyl (e.g. cyclopentylsulfonyl, cyclohexylsulfonyl, etc.), phenyl, naphthyl, mono- or diphenyl-$C_{1-3}$ alkyl (e.g. benzyl, diphenylmethyl, etc.), phenoxy, benzoyl, phenoxycarbonyl, benzylcarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfonyl, phenyl-$C_{1-4}$ alkylsulfonylamino or phenylsulfonylamino which may have 1–4 substituent groups (the substituent groups which may substitute the phenyl or naphthyl moieties of these groups include $C_{1-4}$ alkyl such as methyl, ethyl, propyl, butyl, isopropyl, etc., $C_{1-4}$ alkoxy such as methoxy, ethoxy, n-propyloxy, i-propyloxy, n-butyloxy, etc., halogen such as chloro, bromo, iodo, etc., hydroxy, benzyloxy, amino, said mono- or di-$C_{1-4}$ alkylamino, nitro, said $C_{1-6}$ alkyl-carbonyl, benzoyl, etc.). The number of substituent groups which may be present on each of said $C_{6-14}$ aryl, $C_{7-18}$ aralkyl, $C_{6-14}$ aryl-$C_{2-12}$ alkenyl, $C_{6-14}$ aryl-$C_{2-12}$ alkynyl and $C_{3-7}$ cycloalkyl-$C_{1-6}$ alkyl preferably ranges from 1 to about 5.

In the formula presented hereinbefore, Ar represents a tetracyclic fused heterocyclyl group which may be substituted. As mentioned hereinbefore, the compound of this invention has a unique chemical structure such that a group of the formula

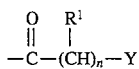

has been attached to a tetracyclic fused heterocycle and, based on this structural characteristic, exhibits potent cholinesterase activity. Therefore, there is no particular limitation on the types of substituents that may be present on the tetracyclic fused heterocycle for Ar, and various substituent groups like those mentioned above for $C_{6-14}$ aryl, $C_{7-18}$ aralkyl, $C_{6-14}$ aryl-$C_{2-12}$ alkenyl, $C_{6-14}$ aryl-$C_{2-12}$ alkynyl, and $C_{3-7}$ cycloalkyl-$C_{1-6}$ alkyl can be employed. The preferred number of such substituent groups is 1–10.

The tetracyclic fused heterocyclyl group Ar is a tetracyclic fused heterocyclic group which may contain 1–8 heteroatoms selected from among e.g. nitrogen, oxygen and sulfur or preferably a tetracyclic fused ring system containing at least one nitrogen-containing heterocycle (preferably a 5- through 8-membered heterocycle containing 1–4 nitrogen atoms). More preferably, a tetracyclic fused heterocyclic system containing an optionally hydrogenated indole or isoindole ring is employed.

The tetracyclic fused heterocyclic system containing the optionally hydrogenated indole or isoindole ring mentioned above may for example be a group available on elimination of one hydrogen atom from any of the tetracyclic fused-ring systems

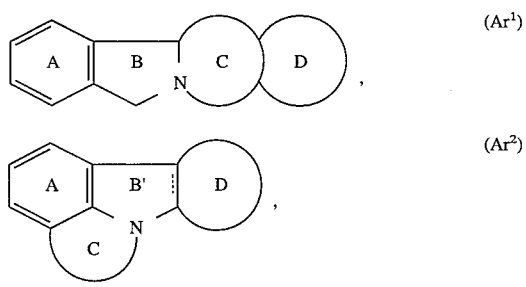

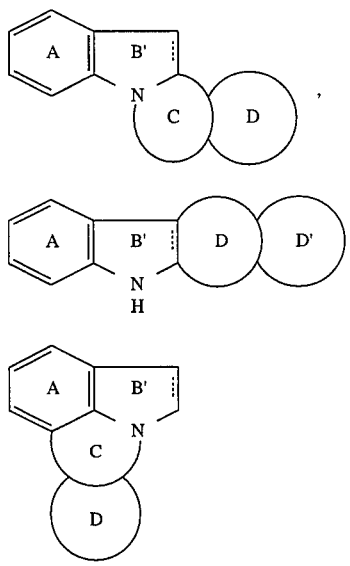

In the above formulas, the fused ring consisting of A and B is an isoindole ring which may be hydrogenated and/or substituted; the fused ring consisting of A and B' is an indole ring which may be hydrogenated and/or substituted; ring C, ring D and ring D' each represents a 5- through 8-membered ring which may be substituted, although the modes of condensation are not limited to those illustrated above.

The benzene ring represented by ring A may have substituent groups such as those mentioned for $R^1$, viz. $C_{6-14}$ aryl, $C_{7-18}$ aralkyl, $C_{6-14}$ aryl-$C_{2-12}$ alkenyl, $C_{6-14}$ aryl-$C_{2-12}$ alkynyl or $C_{3-7}$ cycloalkyl-$C_{1-6}$ alkyl, and the preferred number of such substituents is 1–3. Among the preferred substituents optionally substituted said benzene ring are halogen (e.g. fluoro, chloro), halo-$C_{1-3}$ alkyl (e.g. trifluoromethyl), $C_{1-3}$ alkyl (e.g. methyl), $C_{1-3}$ alkoxy (e.g. methoxy), hydroxy and so on. Particularly preferred are methoxy, hydroxy, and halogen, e.g. fluoro.

The isoindole ring represented by the fused ring consisting of A and B and the indole ring represented by the fused ring consisting of A and B' may each be in the dihydro form and may have substituent groups on the substitutable carbon atoms of ring B or B' or a substituent group on the nitrogen atom of ring B' of said ring system $Ar^4$. Substituent groups that may be present on the ring carbon atoms may for example be the $C_{1-11}$ alkyl, $C_{6-14}$ aryl, $C_{7-18}$ aralkyl groups mentioned for $R^1$, $C_{2-6}$ acyl groups (e.g. as formyl, acetyl, propionyl), halogen (e.g. fluoro, chloro) and oxo. The preferred number of such substituents is 1 or 2. The substituent group that may be present on the nitrogen atom includes the $C_{1-11}$ alkyl, $C_{6-14}$ aryl and $C_{7-18}$ aralkyl groups mentioned for $R^1$, $C_{2-6}$ acyl (e.g. formyl, acetyl, propionyl), halogen (e.g. fluoro, chloro) and oxo, among others. The substituent group or groups optionally substituting ring B or B' are preferably $C_{1-3}$ alkyl (e.g. methyl), $C_{2-4}$ acyl (e.g. acetyl), and oxo. Particularly preferred is oxo.

The "5- through 8-membered ring which may be substituted", represented by ring C, may contain 1 to 3 heteroatoms typically selected from nitrogen, oxygen and sulfur in addition to the nitrogen atom which is a ring member of the "optionally hydrogenated isoindole ring" represented by the fused ring consisting of A and B or the "optionally hydrogenated indole ring" represented by the fused ring consisting of A and B'. The 5- through 8-membered ring mentioned above includes such preferred species as pyrrole, pyridine, dihydropyridine, pyrazine, pyrimidine, imidazole, pyrrolidine, piperidine, azepine, dihydroazepine, tetrahydroazepine, hexahydroazepine (hexamethyleneimine), piperazine, morpholine, thiomorpholine, oxazepine, dihydrooxazepine, tetrahydrooxazepine, hexahydrooxazepine, azocine, dihydroazocine, tetrahydroazocine, hexahydroazocine, octahydroazocine and so on. Particularly preferred are pyrrole, pyrrolidine, piperidine, piperazine, morpholine, tetrahydroazepine, hexahydroazepine (hexamethyleneimine) and so on.

The "5- through 8-membered ring" represented by ring D or ring D' may for example be a 5- through 8-membered heterocycle containing 1 to 3 hetero-atoms typically selected from nitrogen, oxygen and sulfur or a carbocycle. The 5- through 8-membered carbocycle mentioned just above may be a benzene ring or a saturated or unsaturated ring and includes benzene, cyclopentane, cyclopentene, cyclohexane, cyclohexene, cyclohexadiene, cycloheptane, cycloheptene, cycloheptadiene and so on. Where ring D or ring D' has hetero-atoms as ring-constituent members, that is to say it is a heterocycle, it may be whichever of being aromatic or non-aromatic. The aromatic heterocycle may for example be pyridine, furan or thiophene, while the non-aromatic heterocycle is preferably a non-aromatic hetero-ring such as the one mentioned for ring C.

Where said ring D or ring D' is a benzene ring, substituent groups that may optionally substitute the ring include those groups mentioned as optional substituents on ring A.

Thus, the tetracyclic fused heterocyclic group containing an optionally hydrogenated indole or isoindole ring includes groups available on elimination of one hydrogen atom each from the following ring systems and the corresponding dihydro, tetrahydro, hexahydro, octahydro, decahydro and other forms. Specifically, the tetracyclic fuged heterocycle represented by the formula ($Ar^1$) includes, among others, 2H-isoindolo[2,1-e]purine, 1H-pyrazolo-[4',3':3,4]pyrido[2,1-a]isoindole, 1H-pyrido-[2',3':4,5]imidazo[2,1-a]isoindole, 2H,6H-pyrido-[1',2':3,4]imidazo[5,1-a]isoindole, 1H-isoindolo[2,1-a]benzimidazole, 1H-pyrido[3',4':4,5]pyrrolo[2,1-a]isoindole, 2H-pyrido[4',3':4,5]pyrrolo[2,1-a]isoindole, 1H-isoindolo[2,1-a]indole, 2H-isoindolo[1,2-a]isoindole, 1H-cyclopenta[4,5]pyrimido[2,1-a]isoindole, 2H,4H-pyrano[4',3':4,5][1,3]oxazino[2,3-a]isoindole, 2H-isoindolo[2,1-a][3,1]benzoxazine, 7H-isoindolo[1,2-b][1,3]benzoxazine, 2H-pyrido[2',1':3,4]-pyrazino[2,1-a]isoindole, pyrido[2',3':4,5]pyrimido[2,1-a]isoindole, pyrido[3',2':5,6]pyrimido[2,1-a]-isoindole, 1H-pyrido[1',2':3,4]pyrimido[2,1-a]isoindole, isoindolo[2,1-a]quinazoline, isoindolo[2,1-a]quinoxaline, isoindolo[1,2-a]isoquinoline, isoindolo[2,1-b]isoquinoline, isoindolo[2,1-a]quinoline, 6H-oxazino[3',4':3,4][1,4]diazepino[2,1-a]-isoindole, azepino[2',1':3,4]pyrazino[2,1-a]isoindole, 2H,6H-pyrido[2',1':3,4][1,4]diazepino[2,1-a]isoindole, 1H-isoindolo[1,2-b][1,3,4]benzotriazepine, 2H-isoindolo [2,1-a][1,3,4]benzotriazepine, isoindolo[2,1-d][1,4]benzoxazepine, 1H-isoindolo[2,1-b][2,4]benzodiazepine, 1H-isoindolo[2,1-c][2,3]benzodiazepine, 2H-isoindolo[1,2-a][2,4]-benzodiazepine, 2H-isoindolo[2,1-d][1,4]benzodiazepine, 5H-indolo[2,1-b][3]benzazepine, 2H-isoindolo[1,2-a][2]-benzazepine, 2H-isoindolo[1,2-b][3]benzazepine, 2H-isoindolo[2,1-b][2]benzazepine, 2H-isoindolo[1,2-b][1,3,4]benzooxadiazocine, isoindolo[2,1-b][1,2,6]benzotriazocine, 5H-4,8-methano-1H-[1,5]diazacycloundecino[1,11-a]indole and so on.

The tetracyclic fuged heterocycle represented by the formula ($Ar^2$) includes, among others, 1H,4H-pyrrolo[3',2':4,5]pyrrolo[3,2,1-ij]quinoline, pyrrolo[3,2,1-jk]carbazole, 1H-furo[2',3':4,5]pyrrolo[3,2,1-ij]quinoline, 1H,4H-cyclopenta[4,5]pyrrolo[1,2,3-de]quinoxaline, 1H,4H- cyclopenta[4,5]pyrrolo[3,2,1-ij]quinoline, pyrido[3',4':4,5] pyrrolo[1,2,3-de]benzoxazine, [1,4]oxazino[2,3,4-jk] carbazole, 1H,3H-[1,3]oxazino[5,4,3-jk]carbazole, pyrido [3',4':4,5]-pyrrolo[1,2,3-de][1,4]benzothiazine, 4H-pyrrolo [3,2,1-de]phenanthridine, 4H,5H-pyrido[3,2,1-de] phenanthridine, 1H,4H-3a,6a-diazafluoranthene, 1-oxa-4, 6a-diazafluoranthene, 4-oxa-2,10b-diazafluoranthene, 1-thia-4,6a-diazafluoranthene, 1H-pyrazino[3,2,1-jk]carbazole, 1H-indolo[3,2,1-de][1,5]naphthyridine, benzo[b]pyrano[2,3,4-hi]-indolidine, 1H,3H-benzo[b]pyrano[3,4,5-hi]-indolidine, 1H,4H-pyrano[2',3':4,5]pyrrolo[3,2,1-ij] quinoline, 1H,3H-benzo[b]thiopyrano[3,4,5-hi]indolidine, 1H-pyrido[3,2,1-jk]carbazole, 4H-3-oxa-11b-azacyclohepta [jk]fluorene, 2H-azepino[1',2':1,2]pyrimidino[4,5-b]-indole, 1H,4H-cyclohepta[4,5]pyrrolo[1,2,3-de]-quinoxaline, 5H-pyrido[3',4':4,5]pyrrolo[1,2,3 -ef][1,5]benzoxazepine, 4H-pyrido[3',4':4,5]pyrrolo[3,2,1-jk][4,1]benzothiazepine, 5H-pyrido[3',4':4,5]pyrrolo[1,2,3-ef][1,5]benzothiazepine, 5H-pyrido[4',3':4,5]pyrrolo[1,2,3-ef][1,5]benzothiazepine, [1,2,4]triazepino[6,5,4-jk]carbazole, [1,2,4]triazepino[6,7, 1-jk]carbazole, [1,2,5]triazepino[3,4,5-jk]carbazole, 5H-[1, 4]oxazepino[2,3,4-jk]carbazole, 5H-[1,4]thiazepino[2,3,4-jk]carbazole, [1,4]diazepino[3,2,1-jk]carbazole, [1,4] diazepino[6,7,1-jk]carbazole, azepino[3,2,1-jk]carbazole, 1H-cycloocta[4,5]pyrrolo[1,2,3-de]quinoxaline, 1H-cycloocta[4,5]pyrrolo[3,2,1-ij]quinoline and so on.

The tetracyclic fuged heterocycle represented by the formula (At³) includes, among others, 1H-indolo[1,2-a] benzimidazole, 1H-indolo[1,2-b]indazole, pyrrolo[2',1':3,4] pyrazino[1,2-a]indole, 1H,5H-pyrrolo[1',2':4,5]pyrazino[1, 2-a]indole, 2H-pyrido[[2',3':3,4]pyrrolo[1,2-a]indole, 1H-pyrrolo[2',3':3,4]pyrido[1,2-a]indole, 1H-indolo[1,2-a] indole, 6H-isoindolo[2,1-a]indole, 6H-indolo[1,2-c][1,3] benzoxazine, 1H-indolo[1,2-b][1,2]benzothiazine, pyrimido [4',5':4,5]pyrimido[1,6-a]indole, pyrazino[2',3':3,4]pyrido [1,2-a]indole, 6H-pyrido[1',2':3,4]pyrimido[1,6-a]indole, indolo[1,2-b]cinnoline, indolo[1,2-a]quinazoline, indolo[1, 2-c]quinazoline, indolo[2,1b]quinazoline, indolo[1,2-a]quinoxaline, indolo[1,2-a][1,8]naphthyridine, indolo[1,2-b]-2, 6-naphthyridine, indolo[1,2-b][2,7]naphthyridine, indolo[1, 2-h]-1,7-naphthyridine, indolo[1,2-b]isoquinoline, indolo[2, 1-a]isoquinoline, indolo[1,2-a]quinoline, 2H,6H-pyrido[2', 1':3,4][1,4]diazepino[1,2-a]indole, 1H-indolo[2,1-c][1,4] benzodiazepine, 2H-indolo[1,2-d][1,4]benzodiazepine, 2H-indolo[2,1-a][2,3]benzodiazepine, 2H-indolo[2,1-b][1, 3]benzodiazepine, 1H-indolo[1,2-b][2]benzazepine, 2H-indolo[1,2 -a][1]benzazepine, 2H-indolo[2,1-a][2]benzazepine, indolo[1,2-e][1,5]benzodiazocine, indolo[2,1-b][3] benzazocine and so on.

The tetracyclic fuged heterocycle represented by the formula (Ar⁴) includes, among others, 1H-imidazo[1,40 ,2':1,2]pyrido[3,4-b]indole, 1H-imidazo[1',2':1,6]pyrido[4, 3-b]indole, 1H-imidazo[1',5':1,2]pyrido[3,4-b]indole, 1H-imidazo[1',5':1,6]pyrido[4,3-b]indole, 1H-pyrido[2', 1':2,3]-imidazo[[4,5-b]indole, imidazo[4,5-a]carbazole, imidazo[4,5-c]carbazole, pyrazolo[3,4-c]carbazole, 2H-pyrazino[1',2':1,5]pyrrolo[2,3-b]indole, 1H-pyrrolo[1', 2':1,2]pyrimido[4,5-b]indole, 1H-indolizino[6,7-b]indole, 1H-indolizino[8,7-b]indole, indolo[2,3-b]indole, indolo[3, 2-b]indole, pyrrolo[2,3-a]carbazole, pyrrolo[2,3-b]carbazole, pyrrolo[2,3-c]-carbazole pyrrolo[3,2-a]carbazole, pyrrolo[3,2-b]-carbazole, pyrrolo[3,2-c]carbazole, pyrrolo[3,4-a]-carbazole, pyrrolo[3,4-b]carbazole, pyrrolo[3,4-c]carbazole, 1H-pyrido[3',4':4,5]furo[3,2-b]indole, 1H-furo[3, 4-a]carbazole, 1H-furo[3,4-b]carbazole, 1H-furo[3,4-c] carbazole, 2H-furo[2,3-a]carbazole, 2H-furo[2,3-c] carbazole, 2H-furo[3,2-a]carbazole, 2H-furo[3,2-c] carbazole, 1H-pyrido[3',4':4,5]thieno[2,3-b]indole, thieno [3',2':5,6]thiopyrano[4,3-b]indole, thieno[3',4':5,6]thiopyrano[4,3-b]indole, 1H-[1]-benzothieno[2,3-b]indole, 1H-[1] benzothieno[3,2-b]indole, 1H-thieno[3,4-a]carbazole, 2H-thieno[2,3-b]carbazole, 2H-thieno[3,2-a]carbazole, 2H-thieno[3,2-b]carbazole, cyclopenta[4,5]pyrrolo[2,3-f] quinoxaline, cyclopenta[5,6]pyrido[2,3-b]indole, pyrido[2', 3':3,4]cyclopenta[1,2-b]indole, pyrido[2',3':4,5]cyclopenta [1,2-b]indole, pyrido[3',4':3,4]cyclopenta[1,2-b]indole, pyrido[3',4':4,5]-cyclopenta[1,2-b]indole, pyrido[4',3':4,5] cyclopenta[1,2-b]indole, 1H-cyclopenta[5,6]pyrano[2,3-b] indole, 1H-cyclopenta[5,6]thiopyrano[4,3-b]indole, cyclopenta[a]carbazole, cyclopenta[c]carbazole, indeno[1,2-b] indole, indeno[2,1-b]indole, [1,2,4]triazino[4',3':1,2]pyrido [3,4-b]indole, 1,3,5-triazino[1',2':1,1]pyrido[3,4-b]indole, 1H-[1,4]oxazino[4',3':1,2]pyrido[3,4-b]indole, 1H-[1,4]oxazino[4',3':1,6]pyrido[3,4-b]indole, 4H-[1,3]oxazino[3',4':1, 2]pyrido[3,4-b]indole, indolo[3,2b][1,4]benzoxazine, 1,3-oxazino[6,5-b]carbazole, 2H-pyrimido[2',1':2,3][1,3] thiazino[5,6-b]indole, 2H-[1,3]thiazino[3',2':1,2]pyrido[3,4-b]indole, 4H-[1,3]thiazino[3',4':1,2]pyrido[3,4-b]indole, indolo[2,3-b][1,4]benzothiazine, indolo[3,2-b][1,4]benzothiazine, indolo[3,2-c][2,1]benzothiazine, 1,4-thiazino[2, 3-a]carbazole, [1,4]thiazino[2,3-b]carbazole, [1,4]thiazino [2,3-c]carbazole, 1,4-thiazino[3,2b]carbazole, 1,4-thiazino [3,2-c]carbazole, 1H-indolo[2,3-g]pteridine, 1H-indol o[3, 2-g]pteridine, pyrazino[1',2':1,2]pyrido[3,4-b]indole, pyrazino[1',2':1,2]pyrido[4,3-b]indole, 1H-pyrido [2',3':5,6] pyrazino[2,3-b]indole, 1H-pyrido[3',2':5,6]pyrazino[2,3-b] indole, 1H-pyrido[3',4':5,6]pyrazino[2,3-b]indole, pyrido[1', 2':1,2]pyrimido[4,5b ]indole, pyrido[1',2':1,2]pyrimido[5,4-b]indole, pyrido[2',1':2,3]pyrimido[4,5-b]indole, pyrimido [1',2':1,2]pyrido[3,4-b]indole, pyrimido[1',2':1,6]pyrido[3, 4-b]indole, pyrimido[5',4':5,6]pyrano[2,3-b]indole, pyridazino[4',5':5,6]thiopyrano[4,5-b]indole, 1H-indolo[3, 2-c]cinnoline, 1H-indolo[2,3-b]quinoxaline, 1H-pyrazino[2, 3-a]carbazole, 1H-pyrazino[2,3-b]carbazole, 1H-pyrazino [2,3-c]carbazole, 1H-pyridazino[3,4-c]carbazole, 1H-pyridazino[4,5-b]carbazole, 1H-pyrimido[4,5-a]carbazole, 1H-pyrimido[4,5-c]carbazole, 1H-pyrimido[5,4-a]carbazole, 1H-pyrimido[5,4-b]carbazole, 1H-pyrimido[5,4-c] carbazole, 7H-1,4-dioxino[2',3':5,6]-[1,2]dioxino[3,4-b] indole, 6H-[1,4]benzodioxino[2,3-b]indole, 6H-[1,4] benzodithiino[2,3-b]indole, 1H-indolo[2,3-b]-1,5-naphthyridine, 1H-indolo[2,3-b][1,6]naphthyridine, 1H-indolo[2,3-b][1,S]naphthyridine, 1H-indolo[2,3-c]-1,5-naphthyridine, 1H-indolo[2,3-c][1,6]naphthyridine, 1H-indolo[2,3-c][1,7]-naphthyridine, 1H-indolo[2,3-c][1,8]naphthyridine, 1H-indolo[3,2-b]-1,5-naphthyridine, 1H-indolo [3,2-b][1,7]naphthyridine, 1H-indolo[3,2-b][1,8] naphthyridine, 1H-indolo[3,2-c][1,8]naphthyridine, indolo [2,3a]quinolizine, indolo[2,3-b]quinolizine, indolo[3,2a] quinolizine, indolo [3, 2-b]quinolizine, pyrano [4',3':5,6 ]pyrido[3,4-b]indole, pyrido[4',3':4,5]pyrano[3,2-b]indole, pyrido[4',3':5,6]pyrano[2,3-b]indole, pyrido[4',3':5,6]pyrano[3,4-b]indole, 1H-indolo[2,3c]isoquino line, 1H-indolo [3,2-c]isoquinoline, 1H-indolo[2,3-c]quinoline, 1H-indolo [3,2-c]quinoline, 1H-pyrido [2,3-a]carbazole, 1H-pyrido[2, 3-b]carbazole, 1H-pyrido [2,3-c]carbazole, 1H-pyrido[3,2-a]carbazole, 1H-pyrido [3,2-b]carbazole, 1H-pyrido[3,2-c] carbazole, 1H-pyrido [3,4-a]carbazole, 1H-pyrido [3,4-b] carbazole, 1H-pyrido [3,4-c]carbazole, 1H-pyrido[4,3-a] carbazole, 1H-pyrido [4,3-b]carbazole, 1H-pyrido[4,3-c] carbazole, 1H-quindo line , 1H-quinindoline, 1H-pyrano[3', 4':5,6]pyrano [4,3-b]indole, [1]benzopyrano[2,3-b]indole, [1]benzopyrano[3,2-b]indole, [1]benzopyrano[3,4-b]indole, [1]benzopyrano[4,3-b]indole, [2]benzopyrano [4,3-b]indole, pyrano[2,3-a]carbazole, pyrano[2,3-b]carbazole, pyrano[2,3-c]carbazole, pyrano[3,2a]carbazole, pyrano[3,2-c]carbazole, pyrano[3,4a]carbazole, 1H-phosphinolino[4,3-b]indole, [1]benzothiopyrano[2,3-b]indole, [1]benzothiopyrano[3,2-b]indole, [1]benzothiopyrano[3,4-b]indole, [1]benzothiopyrano[4,3-b]indole, [2]benzothiopyrano[4,3-b]indole, 1H-benzo[a]carbazole, 1H-benzo[b]carbazole, 1H-benzo[c]carbazole, [1,6,2]oxathiazepino[2',3':1,2]pyrido[3,4-b]indole, 1H-azepino[1',2':1,2]pyrido[3,4-b]indole, 1H-pyrido[1',2':1,2]azepino[4,5-b]indole, 2H-pyrido[1',2':1,2]azepino[3,4-b]indole, 1H-pyrido[3',2':5,6]oxepino[3,2-b]indole, 1H-pyrido[4',3':5,6]oxepino[3,2-b]indole, 2H-pyrido[2',3':5,6]oxepino[2,3-b]indole, 2H-pyrido[2',3':5,6]oxepino[3,2-b]indole, 2H-pyrido[3',4':5,6]oxepino[3,2-pyrido[2',3':4,5]cyclohepta[1,2-b]indole, b]indole, pyrido[3',2':3,4]cyclohepta[1,2-b]indole, pyrido[3',4':4,5]cyclohepta[1,2-b]indole, pyrido[3',4':5,6]cyclohepta[1,2-b]indole, 2H-pyrano[3',2':2,3]azepino[4,5-b]indole, 1H-indolo[3,2b][1,5]benzoxazepine, 1H-indolo[3,2-d][1,2]benzoxazepine, 1H-indolo[2,3-c][1,5]benzothiazepine, [1,4]diazepino[2,3-a]carbazole, indolo[2,3b][1,5]benzodiazepine, indolo[2,3d][1,3]benzodiazepine, indolo[3,2-b][1,4]benzodiazepine, indolo[3,2-b][1,5]benzodiazepine, indolo[3,2-d][1,3]benzodiazepine, indolo[3,2d][2,3]benzodiazepine, indolo[2,3-a][3]benzazepine, indolo[2,3-c][1]benzazepine, indolo[2,3d][1]benzazepine, indolo[2,3-d][2]benzazepine, indolo[3,2-b][1]benzazepine, indolo[3,2c][1]benzazepine, indolo[3,2-d][1]benzazepine, 1H-indolo[2,1-b][3]benzazepine, 1H-[1]benzoxepino[5,4-b]indole, 1H-[2]benzoxepino[4,3-b]indole, 1H-[1]benzothiepino[4,5-b]indole, 1H-[1]benzothiepino[5,4b]indole, benzo[3,4]cyclohepta[1,2-b]indole, benzo[4,5]cyclohepta[1,2-b]indole, benzo[5,6]cyclohepta[1,2-b]indole, benzo[6,7]cyclohepta[1,2-b]indole, cyclohepta[b]carbazole, 4H-[1,5]oxazocino[5',4':1,6]pyrido[3,4-b]indole, azocino[1',2':1,2]pyrido[3,4-b]indole, 2,6-methano-2H-azecino[4,3-b]indole, 3,7-methano-3H-azecino[5,4 -b]indole, pyrido[1',2':1,8]azocino[5,4-b]indole, pyrido[4',3':6,7]oxocino [2,3-b]indole, pyrido[4',3':6,7]oxocino [4,3-b]indole, 1,5-methano-1H-azecino[3,4-b]indole, 2, 6-methano-1H-azecino[5,4b]indole, 1H-pyrido[3',4':5,6]cycloocta[1,2-b]indole, 1,4-ethanooxocino[3,4-b]indole, pyrano[3',4':5,6]cycloocta[1,2-b]indole, 1H-indolo[2,3-c][1,2,5,6]benzotetrazocine, 1H-indolo[2,3c][1,6]benzodiazocine, 6,13b-methano-13bH-azecino[5,4-10 b]indole, oxocino[3,2-a]carbazole, 1H-benzo[g]cycloocta[b]indole, 6,3-(iminomethano)-2H-1,4-thiazonino[9,8-b]indole, 1H,3H[1,4 1oxazonino[4',3':1,2]pyrido[3,4-b]indole, 2H-3,6ethanoazonino[5,4-b]indole, 2H-3,7-methanoazacycloundecino[5,4-b]indole, 1H-6,12b-ethanoazonino[5,4-b]indole, indolo[3,2-e][2]benzazonine, 5,9methanoazacycloundecino[5,4-b]indole, 3,6-ethano-3H-azecino[5,4-b]indole, 3,7-methano-3H-azacycloundecino[5,4-b]indole, pyrano[4',3':8,9]azecino[5,4-b]indole, 1H-indolo[2,3-c][1,7]benzodiazecine, 1H-indolo[3,2-e][2]benzazecine and so on.

Furthermore, such tetracyclic fused heterocycles are preferred as benzo[e]pyrrolo[3,2-b]indole, benzo[e]pyrrolo[3,2-g]indole, benzo[e]pyrrolo[3,2,1-hi]indole, benzo[e]pyrrolo[3,4-b]indole, benzo[g]pyrrolo[3,4-b]indole, 1H-benzo[f]pyrrolo[1,2a]indole, 1H-benzo[g]pyrrolo[1,2-a]indole, 2H-benzo[e]pyrrolo[1,2-a]indole, 1H-benzo[f]pyrrolo[2,1a]isoindole, 1H-benzo[g]pyrrolo[2,1-a]isoindole, 2H-benzo[e]pyrrolo[2,1-a]isoindole, isoindolo[6,7,1cde]indole, spiro[cyclohexane-1,5'-[5H]pyrrolo[2,1a]isoindole], isoindolo[7,1,2-hij]quinoline, 7,11methanoazocino[1,2-a]indole, 7,11-methanoazocino[2,1a]isoindole, dibenz[cd,f]indole, dibenz[cd,g]indole, dibenz[d,f]indole, 1H-dibenz[e,g]indole, 1H-dibenz[e,g]isoindole, naphtho[1,2,3-cd]indole, naphtho[1,8-ef]indole, naphtho[1,8-fg]indole, naphtho[3,2,1-cd]indole, 1H-naphtho[1,2-e]indole, 1H-naphtho[1,2-f]indole, 1H-naphtho[1,2-g]indole, 1H-naphtho[2,1-e]indole, 1H-naphtho[2,3-e ]indole, 1H-naphtho[1,2-f]isoindole, 1H-naphtho[2,3-e]isoindole, spiro[1H-carbazole-1,1'-cyclohexane], spiro[2H-carbazole-2,1'-cyclohexane], spiro[3H-carbazole-3,1'-cyclohexane], cyclohepta[4,5]pyrrolo[3,2-f]quinoline, cyclohepta[4,5]pyrrolo[3,2-h]quinoline, azepino[4,5-b]benz[e]indole, 1H-azepino[1,2-a]benz[f]indole, 1H-azepino[2,1-a]benz[f]isoindole, benzo[e]cyclohepta[b]indole, benzo[g]cyclohepta[b]indole and so on.

The tetracyclic fuged heterocycle represented by the formula (Ar⁵) includes, among others, 1H-dipyrrolo[2,3-b:3',2',1'-hi]indole, spiro[cyclopentan-1,2' (1'H)-pyrrolo[3,2,1-hi]indole], spiro[imidazoridine-4,1' (2'H)-[4H]pyrrolo [3,2,1-ij ]quinoline], pyrido[2,3-b]pyrrolo [3,2,1-hi]indole, pyrido[4,3-b]pyrrolo[3,2,1-hi]indole, benzo[de]pyrrolo[3,2,1-ij]quinoline, 3H-pyrrolo[3,2,1-de]acridine, 1H-pyrrolo[3,2,1-de]phenanthridine, spiro[cyclohexane-1,6'-[6H]pyrrolo [3,2,1-ij]quinoline], 4,9-methanopyrrolo[3,2,1-1m][1]benzoazocine, spiro[cycloheptane-1,6'-[6H]pyrrolo[3,2,1-ij]quinoline], 1H-pyrano[3,4-d]pyrrolo[3,2,1-jk][1]benzazepine, 3H-benzo[b]pyrrolo[3,2,1-jk][4,1]benzothiazepine, 7H-indolo[1,7-ab][4,1]benzoxazepine, benzo[b]pyrrolo[3,2,1-jk][1,4]benzodiazepine, indolo[1,7-ab][1,4]benzodiazepine, indolo[1,7-ab][1]benzazepine, indolo[7,1-ab][3]benzazepine, 1H-cyclohepta[d]pyrrolo[3,2,1-jk][1]benzazepine, spiro[azepino[3,2,1-hi]indole-7(4H), 1'-cycloheptane], 4H-5,11-methanopyrrolo[3,2,1-no][1]benzazacycloundecine, spiro[azepino[3,2,1 -hi]indole-7(4H),1'-cyclooctane] and so on.

The tetracyclic fused heterocyclic group Ar includes not only the above-mentioned tetracyclic fused heterocyclic groups containing an optionally hydrogenated indole or isoindole ring but also the groups available on elimination of one hydrogen atom each from the following tetracyclic fused heterocycles and the corresponding dihydro, tetrahydro, hexahydro, octahydro and decahydro forms. Thus, fluoranthene, acephenanthrylene, aceanthrylene, triphenylene, pyrene, chrysene, naphthacene, pleiadene, benzo[a]anthracene, indeno[1,2-a]indene, cyclopenta[a]phenanthrene, pyrido[1',2':1,2]imidazo[4,5-b]quinoxaline, 1H-2-oxapyrene, spiro[piperidine-4.9'-xanthene], etc. are preferred.

Particularly preferred examples of Ar are the groups available on elimination of one hydrogen atom each from the tetracyclic fused heterocycles of the following formulas.

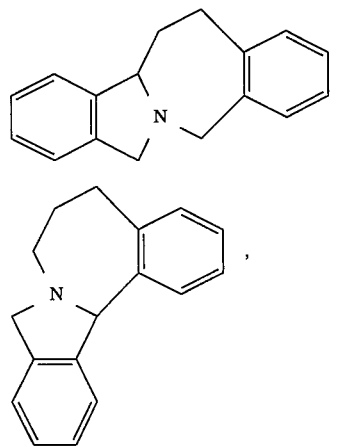

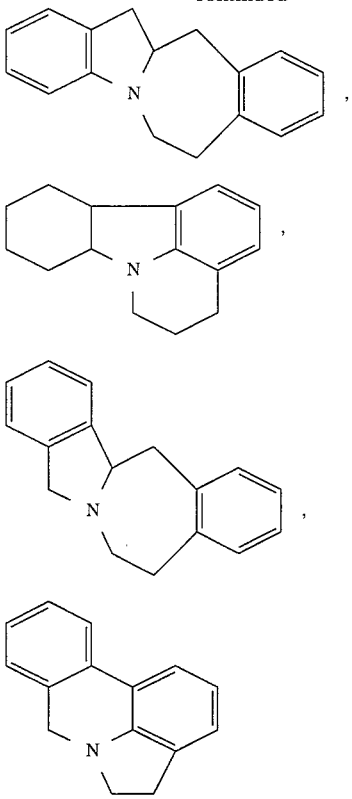

The rings C, D and D' may each have substituents which may be present on any carbon atoms of the respective rings. Among such substituents, which may number 1 through 5, are halogen (e.g. fluoro, chloro, bromo, iodo), nitro, cyano, oxo, hydroxy, $C_{1-4}$ alkoxy (e.g. methoxy, ethoxy, propyloxy, butyloxy, isopropyloxy, etc.), $C_{1-4}$ alkylthio (e.g. methylthio, ethylthio, propylthio, etc.), amino, mono- or di-$C_{1-4}$ alkylamino (e.g. methylamino, ethylamino, propylamino, dimethylamino, diethylamino, etc.), 5- through 7-membered cycloamino which may have 1–3 hetero-atoms selected from among N, O and S in addition to the amino nitrogen and carbon atoms (e.g. pyrrolidino, piperidino, morpholino, thiomorpholino, etc.), $C_{1-4}$ alkyl-carbonylamino (e.g. acetylamino, propionylamino, butyrylamino, etc.), $C_{1-4}$ alkylsulfonylamino (e.g. methylsulfonylamino, ethylsulfonylamino, etc.), $C_{1-4}$ alkoxy-carbonyl (e.g. methoxycarbonyl, ethoxycarbonyl, propoxycarbonyl, etc.), carboxyl, $C_{1-6}$ alkyl-carbonyl (e.g. methylcarbonyl, ethylcarbonyl, propylcarbonyl, etc.), carbamoyl, mono- or di-$C_{1-4}$ alkylcarbamoyl (e.g. methylcarbamoyl, ethylcarbamoyl, etc.), $C_{1-6}$ alkylsulfonyl (e.g. methylsulfonyl, ethylsulfonyl, propylsulfonyl, etc.) and so on.

Where ring C, ring D or ring D' has a ring-constituent nitrogen atom, there may be a substituent group on the nitrogen atom. Thus, ring C, ring D and ring D' may have

>N—$R^6$ $R^6$ represents a hydrogen atom, a hydrocarbon group which may be substituted or an acyl group which may be substituted in the respective rings.

The hydrocarbon group which may be substituted, as represented by $R^6$, may be any of those hydrocarbon groups which may be substituted as mentioned for $R^1$. Among such groups, $C_{1-7}$ alkyl (e.g. methyl, ethyl, n-propyl, etc.) or $C_{7-10}$ aralkyl (e.g. phenylmethyl, phenylethyl, etc.), which may be substituted by 1–3 substituent groups such as halogen (e.g. fluoro, chloro, etc.), $C_{1-4}$ alkoxy (e.g. methoxy, ethoxy, etc.), hydroxy, etc., are preferred, particularly preferred is an unsubstituted benzyl group.

Y represents an unsubstituted or substituted amino group or a nitrogen-containing saturated heterocyclic group which may be substituted.

The "unsubstituted or substituted amino group" as represented by Y includes groups of the formula

(VII)

wherein $R^{2'}$ and $R^{3'}$ are the same or different and each represents a hydrogen atom, a hydrocarbon group which may be substituted or an acyl group which may be substituted, among others.

The hydrocarbon group which may be substituted, as represented by $R^{2'}$ and $R^{3'}$, includes the hydrocarbon groups which may be substituted as mentioned for $R^1$.

Preferred examples of the hydrocarbon group which may be substituted for $R^{2'}$ and $R^{3'}$ are straight-chain or branched $C_{1-11}$ alkyl groups, preferably $C_{1-7}$ alkyl (e.g. methyl, ethyl, n-propyl, i-propyl, n-butyl, i-butyl, tert-butyl, n-pentyl, n-hexyl, etc.), or $C_{7-18}$ aralkyl groups (e.g. phenyl($C_{1-12}$)alkyl such as phenylmethyl, phenylethyl, phenylpropyl, phenylhexyl, etc. and naphthyl($C_{1-8}$)alkyl such as α-naphthylmethyl), preferably $C_{7-10}$ aralkyl (e.g. phenylmethyl, phenylethyl, phenylpropyl), all of which may be respectively substituted by 1–3 substituent groups selected from among e.g. halogen (e.g. fluoro, chloro), $C_{1-4}$ alkoxy (e.g. methoxy, ethoxy), hydroxy and so on.

The "acyl" of the "acyl group which may be substituted" for $R^6$, $R^2$, and $R^3$, includes carboxylic acid-derived acyl groups (e.g. formyl, $C_{2-8}$ alkyl-carbonyl such as acetyl, propionyl, butyryl, benzoyl, and phenylcarbonyl, etc.), sulfonic acid-derived acyl groups (e.g. $C_{1-7}$ alkylsulfonyl such as methanesulfonyl, ethanesulfonyl, propanesulfonyl, benzenesulfonyl, p-toluenesulfonyl, and phenylsulfonyl, etc.), phosphonic acid-derived acyl (e.g. $C_{1-7}$ alkylphosphonyl such as methanephosphonyl, ethanephosphonyl, propanephosphonyl, benzenephosphonyl, p-toluenephosphonyl, and phenyl-phosphonyl, etc.), substituted oxycarbonyl (e.g. $C_{2-8}$ alkyloxycarbonyl or $C_{7-8}$ aralkyloxycarbonyl, such as methyloxycarbonyl, tert-butyloxycarbonyl, benzyloxycarbonyl, etc.). Particularly preferred is $C_{2-8}$ alkyloxycarbonyl.

The substituent group which may substitute the above-mentioned acyl group includes halogen (e.g. fluoro, chloro, bromo, iodo), nitro, hydroxy, amino, mono- or di-$C_{1-6}$ alkylamino (e.g. methylamino, ethylamino, dimethylamino, diethylamino, etc.) and $C_{1-4}$ alkoxy (e.g. methoxy, ethoxy, propoxy, etc.). These substituent groups may number 1–3, preferably 1–2.

Preferred examples of $R^{2'}$ and $R^{3'}$ are straight-chain or branched $C_{1-7}$ alkyl groups (e.g. methyl, ethyl, n-propyl, i-propyl, n-butyl, i-butyl, tert-butyl, n-pentyl, n-hexyl, etc.) or $C_{7-10}$ aralkyl groups (e.g. benzyl, phenylethyl, phenylpropyl, etc.). particularly preferred are $C_{1-3}$ alkyl (e.g. methyl, ethyl) and $C_{7-10}$ aralkyl (e.g. phenylmethyl).

The "nitrogen-containing saturated heterocyclic group" for said "nitrogen-containing saturated heterocyclic group which may be substituted", as represented by Y, includes 5- through 9-membered nitrogen-containing saturated heterocyclic groups which may contain 1–3 hetero-atoms, such as nitrogen, oxygen and sulfur, in addition to the carbon atoms and one nitrogen atom. This nitrogen-containing saturated heterocyclic group may be a group bonding through a ring-constituent nitrogen atom or a group bonding through a ring-constituent carbon atom. The group bonding through a ring-constituent nitrogen atom includes groups of the formula

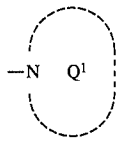

(Y¹)

(wherein ring $Q^1$ represents a 5- through 9-membered nitrogen-containing saturated heterocyclic group which may contain 1–2 hetero-atoms typically selected from nitrogen, oxygen and sulfur in addition to carbon atoms and one nitrogen atom). Specifically, the following groups are preferred.

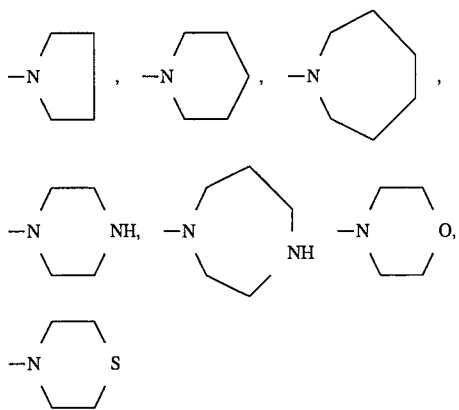

The group bonding through the ring-constituent carbon atom includes groups of the formula.

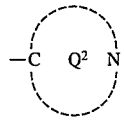

(Y²)

(wherein ring $Q^2$ represents a 5- through 9-membered nitrogen-containing saturated heterocyclic group which may contain 1–2 hetero-atoms typically selected from nitrogen, oxygen and sulfur in addition to carbon atoms and one nitrogen atom), among others. Specifically, the following groups can be mentioned as typical examples.

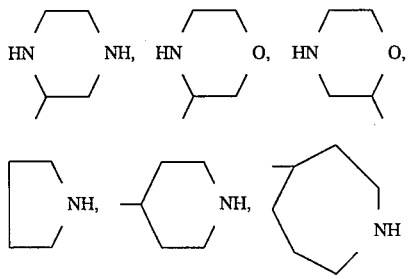

The substituent group which may substitute said "nitrogen-containing saturated heterocyclic group" includes, among others, the hydrocarbon groups which may be substituted as previously mentioned for $R^1$, the acyl groups which may be substituted as previously mentioned for $R^{2'}$ and $R^{3'}$, halogen (e.g. fluoro, chloro, bromo, iodo), nitro, cyano, oxo, hydroxy, $C_{1-4}$ alkoxy (e.g. methoxy, ethoxy, propyloxy, butyloxy, isopropyloxy, etc.), $C_{1-4}$ alkylthio (e.g. methylthio, ethylthio, propylthio, isopropylthio, etc.), amino, mono- or di-$C_{1-4}$ alkylamino (e.g. methylamino, ethylamino, propylamino, dimethylamino, diethylamino, etc.), 5- through 7-membered cycloamino which may have 1–3 hetero-atoms typically selected from N, O and S in addition to the amino nitrogen and carbon atoms (e.g. pyrrolidino, piperidino, morpholino, thiomorpholino, etc.), $C_{1-4}$ alkyl-carbonylamino (e.g. acetylamino, propionylamino, butyrylamino, etc.), $C_{1-4}$ alkylsulfonylamino (e.g. methylsulfonylamino, ethylsulfonylamino, etc.), $C_{1-4}$ alkoxy-carbonyl which may be substituted by nitrophenyl, etc. (e.g. methoxycarbonyl, ethoxycarbonyl, propoxycarbonyl, (4-nitrophenyl)methoxycarbonyl, etc.), phenyl-$C_{1-4}$ alkyloxycarbonyl (e.g. benzyloxycarbonyl etc.), carboxyl, $C_{1-6}$ alkyl-carbonyl (e.g. methylcarbonyl, ethylcarbonyl, propylcarbonyl, etc.), benzoyl which may be substituted by 1 to 3 substituents selected from $C_{1-4}$ alkyl (e.g. methyl, ethyl), halogen (e.g. fluoro, chloro, bromo), $C_{1-4}$ alkoxy (e.g. methoxy, ethoxy), mono- or di-$C_{1-4}$ alkylamino (e.g. methylamino, dimethylamino), 5- through 7-membered cycloamino (e.g. piperidino, morpholino, etc.), nitro and hydroxy; inclusive of such species as 4-fluorobenzoyl, 3,4-dimethoxybenzoyl, etc., carbamoyl, mono- or di-$C_{1-4}$ alkylcarbomoyl (e.g. methylcarbamoyl, ethylcarbamoyl, etc.), $C_{1-6}$ alkylsulfonyl (e.g. methylsulfonyl, ethylsulfonyl, propylsulfonyl, etc.) and so on. These substituents may be present in 1–5 positions. Among these substituents, the hydrocarbon groups which may be substituted as previously mentioned for $R^1$ are preferred. Thus, for example, straight-chain or branched $C_{1-11}$ alkyl groups, preferably straight-chain or branched $C_{1-7}$ alkyl (e.g. methyl, ethyl, n-propyl, i-propyl, n-butyl, tert-butyl, n-pentyl, n-hexyl, etc.), $C_{7-18}$ aralkyl groups (e.g. phenyl($C_{1-12}$) alkyl such as phenylmethyl, phenylethyl, phenylpropyl, phenylhexyl, etc. and naphthyl($C_{1-8}$)alkyl such as α-naphthylmethyl), preferably $C_{7-10}$ aralkyl (e.g. phenylmethyl, phenylethyl, phenylpropyl, etc.), and diphenyl($C_{1-3}$)alkyl groups (e.g. diphenylmethyl), each optionally substituted by e.g. halogen (e.g. fluoro, chloro, bromo, iodo), nitro, $C_{1-4}$ alkoxy (e.g. methoxy, ethoxy), hydroxy, etc., can be mentioned. The position of substitution may be on the carbon or/and nitrogen atoms of the nitrogen-containing saturated heterocycle.

Referring to the formula presented hereinbefore, $R^1$ is preferably a hydrogen atom.

The benzene ring represented by ring A is preferably unsubstituted.

Ar is preferably one of the following groups.

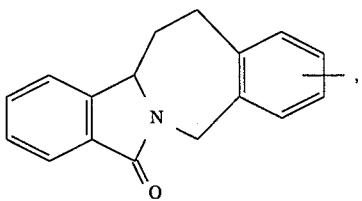

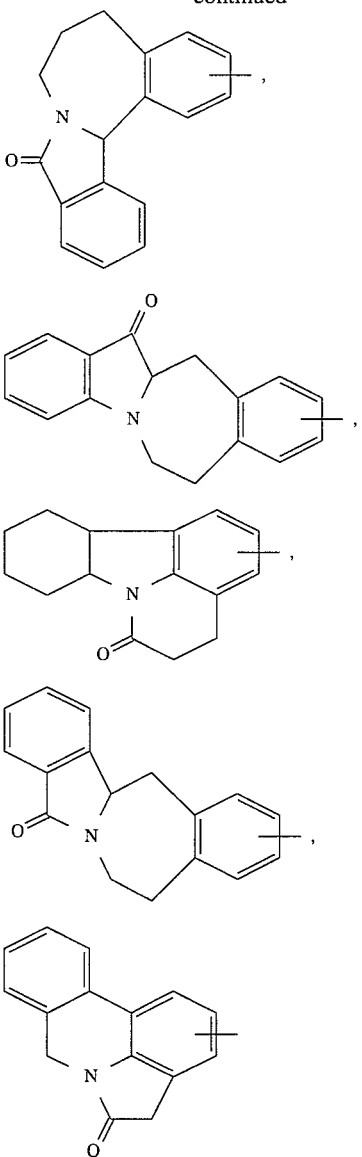

Y is preferably a group of the formula (VII) [particularly where one of $R^{2'}$ and $R^{3'}$ is a straight-chain or branched $C_{1-7}$ alkyl group (e.g. methyl, ethyl, n-propyl, i-propyl, n-butyl, i-butyl, tert-butyl, n-pentyl, n-hexyl) with the other being a $C_{7-10}$ aralkyl group (e.g. phenylmethyl, phenylethyl, phenylpropyl)]or any of pyrrolidine, piperidine, piperazine, morpholine, 1,2,3,4-tetrahydroquinoline, 1,2,3,4-tetrahydroisoquinoline, 2,3,4,5-tetrahydro-1H-1-benzazepine, 2,3,4,5-tetrahydro-1H-2-benzazepine, 2,3,4,5-tetrahydro-1H-3-benzazepine, etc. as substituted by e.g. benzyl which may be substituted. Particularly preferred is any of pyrrolidine, piperidine, piperazine and morpholine as substituted by benzyl which may be substituted. Still more desirable, among them, are 1- or 4-piperidinyl and 1-piperazinyl group substituted by benzyl which may be substituted. The substituent on the benzyl group is preferably halogen (e.g. fluoro, chloro), $C_{1-4}$ alkyl (e.g. methyl, ethyl), $C_{1-4}$ alkoxy (e.g. methoxy), hydroxy, nitro, amino or cyano.

Preferably n stands for a whole number of 2–6, expecially 2.

Specifically, the following compounds meeting the definition of compound (I) and their salts are preferred.

TABLE 1

$$Ar-\overset{O}{\underset{\|}{C}}(CH_2)_n-Y$$

| No. | Ar | n | Y |
|-----|----|----|----|
| 1 |  | 1 |  N—CH₂Ph |

TABLE 1-continued $$\text{Ar}-\overset{\overset{\text{O}}{\|}}{\text{C}}(\text{CH}_2)_n\text{Y}$$

| No. | Ar | n | Y |
|---|---|---|---|
| 2 | (tetracyclic isoindolone-benzazepine) | 2 | piperidine N—CH₂Ph |
| 3 | (tetracyclic isoindolone-benzazepine) | 3 | piperidine N—CH₂Ph |
| 4 | (tetracyclic isoindolone-benzazepine) | 4 | piperidine N—CH₂Ph |
| 5 | (tetracyclic isoindolone-benzazepine) | 5 | piperidine N—CH₂Ph |
| 6 | (tetracyclic isoindolone-benzazepine) | 6 | piperidine N—CH₂Ph |
| 7 | (tetracyclic isoindolone-benzazepine) | 2 | piperidine NH |
| 8 | (tetracyclic isoindolone-benzazepine) | 2 | piperidine N—CH₃ |
| 9 | (tetracyclic isoindolone-benzazepine) | 2 | piperidine N—Et |

TABLE 1-continued $$Ar-\overset{O}{\underset{\|}{C}}-(CH_2)_n-Y$$

| No. | Ar | n | Y |
|---|---|---|---|
| 10 | [tricyclic isoindolinone-benzazepine structure] | 2 | [4-piperidinyl]-N-CH(CH₃)₂ |
| 11 | [tricyclic isoindolinone-benzazepine structure] | 2 | [4-piperidinyl]-N-CH₂-cyclohexyl |

TABLE 2

| No. | Ar | n | Y |
|---|---|---|---|
| 12 | [tricyclic isoindolinone-benzazepine structure] | 2 | [4-piperidinyl]-N-Ac |
| 13 | [tricyclic isoindolinone-benzazepine structure] | 2 | [4-piperidinyl]-N-CO₂CH₃ |
| 14 | [tricyclic isoindolinone-benzazepine structure] | 2 | [4-piperidinyl]-N-CO₂Et |
| 15 | [tricyclic isoindolinone-benzazepine structure] | 2 | [4-piperidinyl]-N-CO₂-CH₂-(4-NO₂-phenyl) |
| 16 | [tricyclic isoindolinone-benzazepine structure] | 2 | [4-piperidinyl]-N-CH₂-(2-CH₃-phenyl) |

TABLE 2-continued

| No. | Ar | n | Y |
|---|---|---|---|
| 17 | (tetracyclic lactam structure) | 2 | 4-(3-methylbenzyl)piperidin-1-yl |
| 18 | (tetracyclic lactam structure) | 2 | 4-(4-methylbenzyl)piperidin-1-yl |
| 19 | (tetracyclic lactam structure) | 2 | 4-(2-fluorobenzyl)piperidin-1-yl |
| 20 | (tetracyclic lactam structure) | 2 | 4-(3-fluorobenzyl)piperidin-1-yl |
| 21 | (tetracyclic lactam structure) | 2 | 4-(4-fluorobenzyl)piperidin-1-yl |
| 22 | (tetracyclic lactam structure) | 2 | 4-(2-chlorobenzyl)piperidin-1-yl |
| 23 | (tetracyclic lactam structure) | 2 | 4-(3-chlorobenzyl)piperidin-1-yl |

TABLE 3

| No. | Ar | n | Y |
|---|---|---|---|
| 24 | (tricyclic isoindolinone-benzazepine structure) | 2 | 4-[(4-chlorobenzyl)]piperidin-1-yl (piperidine N–CH₂–C₆H₄–Cl) |
| 25 | (tricyclic isoindolinone-benzazepine structure) | 2 | 4-[(3-nitrobenzyl)]piperidin-1-yl (piperidine N–CH₂–C₆H₄–NO₂) |
| 26 | (tricyclic isoindolinone-benzazepine structure) | 2 | 4-[(4-hydroxybenzyl)]piperidin-1-yl (piperidine N–CH₂–C₆H₄–OH) |
| 27 | (tricyclic isoindolinone-benzazepine structure) | 2 | 4-[(2-methoxybenzyl)]piperidin-1-yl (piperidine N–CH₂–C₆H₄–OCH₃) |
| 28 | (tricyclic isoindolinone-benzazepine structure) | 2 | 4-benzylpiperidin-1-yl (–N-piperidine-CH₂Ph) |
| 29 | (tricyclic isoindolinone-benzazepine structure) | 2 | 4-benzylpiperazin-1-yl (–N-piperazine-N–CH₂–Ph) |
| 30 | (tricyclic isoindolinone-benzazepine structure) | 1 | 4-(2-phenylethyl)piperazin-1-yl (–N-piperazine-N–CH₂CH₂Ph) |
| 31 | (tricyclic isoindolinone-benzazepine structure) | 3 | 4-phenylpiperazin-1-yl (–N-piperazine-N–Ph) |

TABLE 3-continued

| No. | Ar | n | Y |
|---|---|---|---|
| 32 | [isoindolinone-benzazepine fused structure] | 2 | piperazine-N-CH$_2$-(2-methylphenyl) |
| 33 | [isoindolinone-benzazepine fused structure] | 2 | piperazine-N-CH$_2$-(3-methylphenyl) |
| 34 | [isoindolinone-benzazepine fused structure] | 2 | piperazine-N-CH$_2$-(4-methylphenyl) |
| 35 | [isoindolinone-benzazepine fused structure] | 2 | piperazine-N-CH$_2$-(3-fluorophenyl) |

TABLE 4

| No. | Ar | n | Y |
|---|---|---|---|
| 36 | [isoindolinone-benzazepine fused structure] | 2 | piperazine-N-CH$_2$-(3-chlorophenyl) |
| 37 | [isoindolinone-benzazepine fused structure] | 2 | piperidine-N-CH$_2$-(1-naphthyl) |
| 38 | [isoindolinone-benzazepine fused structure] | 2 | piperidine-N-phenyl |

TABLE 4-continued
| No. | Ar | n | Y |
|---|---|---|---|
| 39 | 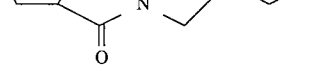 | 2 |  |
| 40 |  | 2 | 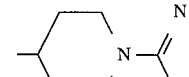 |
| 41 | 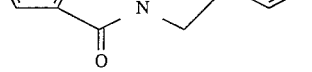 | 2 |  |
| 42 |  | 2 | 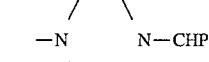 |
| 43 | 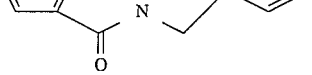 | 2 |  |
| 44 |  | 2 | 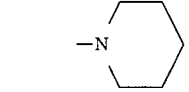 |
| 45 | 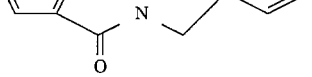 | 2 |  |
| 46 |  | 2 | 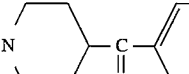 |

TABLE 4-continued

| No. | Ar | n | Y |
|---|---|---|---|
| 47 | (tricyclic isoindolinone-benzazepine structure) | 2 | —N(CH$_3$)$_2$ |

TABLE 5

| No. | Ar | n | Y |
|---|---|---|---|
| 48 | (tricyclic isoindolinone-benzazepine structure) | 2 | —N(C$_2$H$_5$)$_2$ |
| 49 | (tricyclic isoindolinone-benzazepine structure) | 3 | —N(C$_2$H$_5$)(CH$_2$Ph) |
| 50 | (tricyclic isoindolinone-benzazepine structure) | 4 | —N(C$_2$H$_5$)(CH$_2$Ph) |
| 51 | (tricyclic isoindolinone-benzazepine structure) | 5 | —N(C$_2$H$_5$)(CH$_2$Ph) |
| 52 | (tricyclic isoindolinone-benzazepine structure) | 6 | —N(C$_2$H$_5$)(CH$_2$Ph) |
| 53 | (tricyclic isoindolinone-benzazepine structure) | 3 | —N(piperazinyl)-C$_6$H$_4$-CO$_2$H |

TABLE 5-continued

| No. | Ar | n | Y |
|---|---|---|---|
| 54 | [tricyclic isoindolinone-benzazepine with methyl] | 3 | -N(piperazine)N-(2-pyridyl) |
| 55 | [tricyclic isoindolinone-benzazepine with methyl] | 3 | -N(piperazine)N-(2-pyrimidyl) |
| 56 | [tricyclic isoindolinone-benzazepine with methyl] | 3 | -N(piperazine)N-CHPh$_2$ |
| 57 | [tricyclic isoindolinone-benzazepine with methyl] | 3 | -N(piperidine) |
| 58 | [tricyclic isoindolinone-benzazepine with methyl] | 3 | -N(piperidin-4-yl)-C(=O)-C$_6$H$_4$-4-F |
| 59 | [tricyclic isoindolinone-benzazepine with methyl] | 3 | -N(piperidin-4-yl)(OH)(4-chlorophenyl) |

TABLE 6

| No. | Ar | n | Y |
|---|---|---|---|
| 60 | [tricyclic isoindolinone-benzazepine with methyl] | 3 | -N(morpholine)O |

TABLE 6-continued

| No. | Ar | n | Y |
|---|---|---|---|
| 61 | (tricyclic structure) | 3 | -N⟨CH₂CH₂⟩S (thiomorpholine) |
| 62 | (tricyclic structure) | 3 | $-N(CH_3)_2$ |
| 63 | (tricyclic structure) | 3 | $-N(C_2H_5)_2$ |
| 64 | (tricyclic structure, H stereo) | 5 | $-N(C_2H_5)(CH_2Ph)$ |
| 65 | (tricyclic structure, H stereo) | 5 | $-N(C_2H_5)(CH_2Ph)$ |
| 66 | (tricyclic structure, H stereo) | 6 | $-N(C_2H_5)(CH_2Ph)$ |
| 67 | (tricyclic structure) | 6 | $-N(C_2H_5)(CH_2\text{-}2\text{-}CH_3O\text{-}C_6H_4)$ |
| 68 | (tricyclic structure) | 2 | -N(pyrrolidine) |

TABLE 6-continued

| No. | Ar | n | Y |
|---|---|---|---|
| 69 | (fused tricyclic isoindolinone-benzazepine) | 2 | —N-piperidin-4-one |
| 70 | (fused tricyclic isoindolinone-benzazepine) | 2 | —N-piperidine-4-spiro-1,3-dioxolane |
| 71 | (fused tricyclic isoindolinone-benzazepine) | 2 | —N-(2-thiazolyl) |

TABLE 7

| No. | Ar | n | Y |
|---|---|---|---|
| 72 | (fused tricyclic isoindolinone-benzazepine) | 2 | —N-azepane |
| 73 | (fused tricyclic isoindolinone-benzazepine) | 2 | —N-2,3,4,5-tetrahydro-1H-3-benzazepine |
| 74 | (fused tricyclic isoindolinone-benzazepine) | 2 | —N-1,2,3,4-tetrahydroisoquinoline |
| 75 | (fused tricyclic isoindolinone-benzazepine) | 2 | —N-piperazine-N'-Ac |

TABLE 7-continued

| No. | Ar | n | Y |
|---|---|---|---|
| 76 | (tetracyclic lactam structure) | 2 | -N(piperazine)N-CHO |
| 77 | (tetracyclic lactam structure) | 2 | -N(piperazine)N-CH$_2$CH$_2$OH |
| 78 | (tetracyclic lactam structure) | 1 | -N(piperazine)N-CHPh$_2$ |
| 79 | (tetracyclic lactam structure) | 4 | -N(piperazine)N-CHPh$_2$ |
| 80 | (tetracyclic lactam structure) | 4 | -N(piperazine)N-(pyrimidin-2-yl) |
| 81 | (tetracyclic lactam structure) | 5 | -N(piperazine)N-CHPh$_2$ |
| 82 | (tetracyclic lactam structure) | 5 | -N(piperazine)N-(pyrimidin-2-yl) |
| 83 | (tetracyclic lactam structure) | 2 | (piperidine)N-CH$_2$Ph |

TABLE 8

| No. | Ar | n | Y |
|---|---|---|---|
| 84 | (structure) | 2 | −N(piperazine)N−CH₂Ph |
| 85 | (structure) | 2 | (piperidine)N−CH₂Ph |
| 86 | (structure) | 2 | (piperidine)N−CH₂Ph |
| 87 | (structure) | 2 | (piperidine)N−CH₂Ph |
| 88 | (structure) | 2 | −N(piperazine)N−CH₂Ph |
| 89 | (structure) | 2 | (piperidine)N−CH₂Ph |
| 90 | (structure) | 2 | −N(piperazine)N−CH₂Ph |
| 91 | (structure) | 2 | (piperidine)N−CH₂Ph |

TABLE 8-continued

| No. | Ar | n | Y |
|-----|----|----|---|
| 92 | (hexahydrocarbazole-based tricyclic with N-CO-CH2 bridge, methyl on aromatic) | 2 | -N(piperazine)N-CH2Ph |
| 93 | (phenyl-fused benzazepine with C=O, methyl substituent) | 2 | -(piperidin-4-yl)N-CH2Ph |
| 94 | (phenyl-fused benzazepine with C=O, methyl substituent) | 2 | -N(piperazine)N-CH2Ph |
| 95 | (phenyl-fused benzazepine with C=O, methyl substituent) | 2 | -(piperidin-4-yl)N-CH2Ph |

TABLE 9

| No. | Ar | n | Y |
|-----|----|----|---|
| 96 | (phenyl-fused benzazepinone, methyl substituent) | 2 | -N(piperazine)N-CH2Ph |
| 97 | (indoline-fused benzazepinone, methyl substituent) | 2 | -(piperidin-4-yl)N-CH2Ph |
| 98 | (indoline-fused benzazepinone, methyl substituent) | 2 | -N(piperazine)N-CH2Ph |

TABLE 9-continued

| No. | Ar | n | Y |
|-----|----|---|---|
| 99 | (indoline fused benzazepinone) | 2 | 4-(N-CH₂Ph)piperidinyl |
| 100 | (indoline fused benzazepinone) | 2 | 4-(N-CH₂Ph)piperazinyl |
| 101 | (indoline fused benzazepine-dione) | 2 | 4-(N-CH₂Ph)piperidinyl |
| 102 | (indoline fused benzazepine-dione) | 2 | 4-(N-CH₂Ph)piperazinyl |
| 103 | (benzo-carbazole) | 2 | 4-(N-CH₂Ph)piperidinyl |
| 104 | (benzo-carbazole) | 2 | 4-(N-CH₂Ph)piperazinyl |
| 105 | (benzo-carbazole) | 2 | 4-(N-CH₂Ph)piperidinyl |
| 106 | (benzo-carbazole) | 2 | 4-(N-CH₂Ph)piperazinyl |

TABLE 9-continued
| No. | Ar | n | Y |
|---|---|---|---|
| 107 | 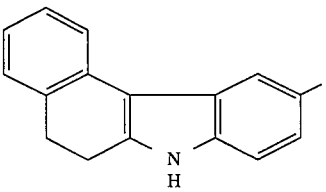 | 2 | 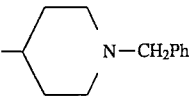 |
TABLE 10
| No. | Ar | n | Y |
|---|---|---|---|
| 108 | 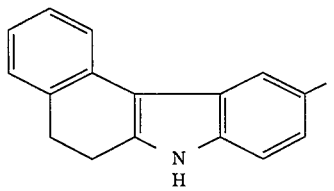 | 2 | 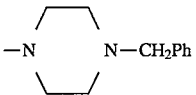 |
| 109 | 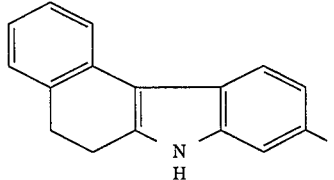 | 2 | 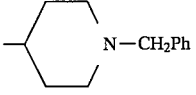 |
| 110 | 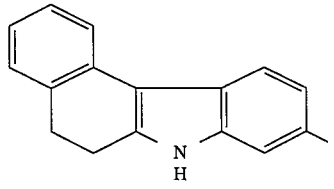 | 2 | 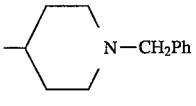 |
| 111 | 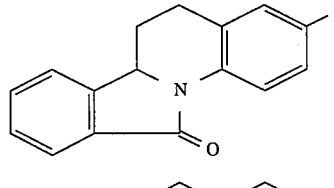 | 2 | 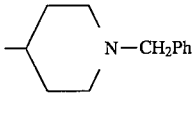 |
| 112 | 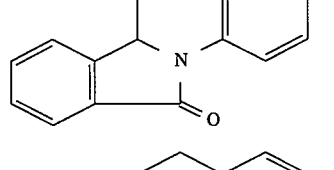 | 2 | 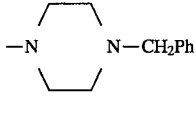 |
| 113 | 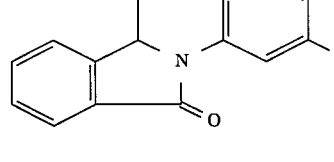 | 2 | 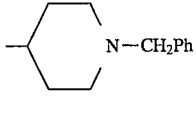 |

TABLE 10-continued

| No. | Ar | n | Y |
|---|---|---|---|
| 114 | (structure) | 2 | −N(piperazine)N−CH₂Ph |
| 115 | (structure) | 2 | (piperidine)N−CH₂Ph |
| 116 | (structure) | 2 | −N(piperazine)N−CH₂Ph |
| 117 | (structure) | 2 | (piperidine)N−CH₂Ph |
| 118 | (structure) | 2 | −N(piperazine)N−CH₂Ph |
| 119 | (structure) | 2 | (piperidine)N−CH₂Ph |

TABLE 11

| No. | Ar | n | Y |
|---|---|---|---|
| 120 | (structure) | 2 | (piperidine)N−CH₂Ph |
| 121 | (structure) | 2 | −N(piperazine)N−CH₂−(3-cyanophenyl) |

TABLE 11-continued
| No. | Ar | n | Y |
|---|---|---|---|
| 122 | 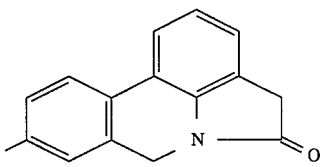 | 2 | 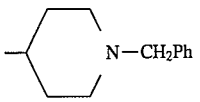 |
| 123 | 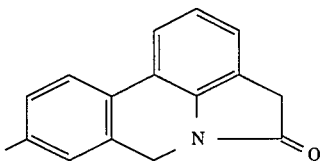 | 2 | 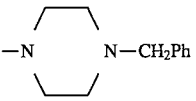 |
| 124 | 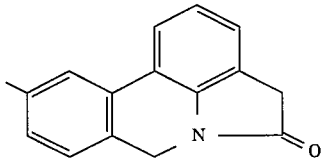 | 2 | 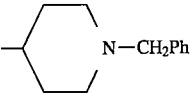 |
| 125 | 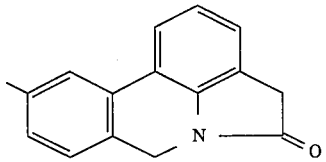 | 2 | 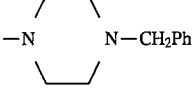 |
| 126 | 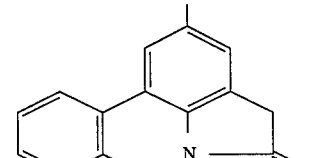 | 2 | 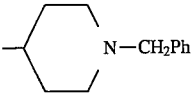 |
| 127 | 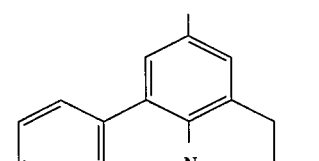 | 2 | 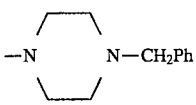 |
| 128 | 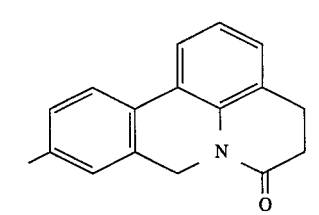 | 2 | 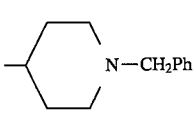 |
| 129 | 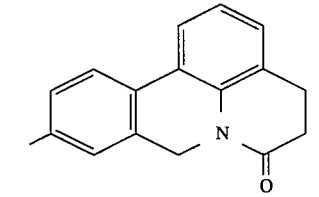 | 2 | 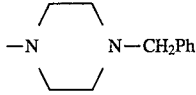 |

TABLE 11-continued

| No. | Ar | n | Y |
|---|---|---|---|
| 130 | (structure) | 2 | piperidine-N—CH₂Ph |
| 131 | (structure) | 2 | —N(piperazine)N—CH₂Ph |

TABLE 12

| No. | Ar | n | Y |
|---|---|---|---|
| 132 | (structure) | 2 | piperidine-N—CH₂Ph |
| 133 | (structure) | 2 | —N(piperazine)N—CH₂Ph |
| 134 | (structure) | 2 | piperidine-N—CH₂Ph |
| 135 | (structure) | 2 | —N(piperazine)N—CH₂Ph |
| 136 | (structure) | 2 | —N(piperazine)NH |

In the above table, Ac stands for acetyl, Et for ethyl, and Ph for phenyl.

The salt of compound (I) according to this invention is preferably a physiologically acceptable acid addition salt. Among such salts are salts with inorganic acids (e.g. hydrochloric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

Where the compound (I) has an acidic group such as —COOH, it may form salts with inorganic bases (e.g. sodium, potassium, calcium, magnesium, ammonium) or salts with organic bases (e.g. triethylamine) and such salts are also subsumed in the object compound of this invention.

The method for production of compound (I) or a salt thereof is now described.

While the following production processes apply to both the production of compound (I) and that of its salt, reference is made only to compound (I) in the following description.

The compound (I) can be produced by reacting a compound of the formula $$Ar-H \qquad (II)$$

wherein Ar has the same meaning as defined hereinbefore, or a salt thereof with a compound of the formula $$Z^1-\overset{O}{\underset{\|}{C}}-(CH)_n-Y \qquad (III)$$
$$\phantom{Z^1-C-}\overset{|}{R^1}\phantom{-(CH)_n-Y}$$

wherein $Z^1$ represents a leaving group; the other symbols have the same meanings as defined hereinbefore, or a salt thereof.

The leaving group $Z^1$ includes halogen (e.g. chloro, bromo, iodo), $C_{1-6}$ alkylsulfonyloxy (e.g. methanesulfonyloxy, ethanesulfonyloxy) and $C_{6-10}$ arylsulfonyloxy (e.g. benzenesulfonyloxy, p-toluenesulfonyloxy), among others, Particularly preferred is halogen (e.g. chloro).

The compound (II) or a salt thereof can be produced by the per se known processes or any processes analogous thereto. Thus, for example, the processes described in J. Chem. Soco, Perkin Trans 1 , 1547 (1979), Chem. Pharm. Bull., 38, 3024 (1990), J. Org. Chem., 37, 3755 (1972), J. Med. Chem., 14, 448 (1971), JP-A-5(1993)-502659, etc. and modifications of such processes can be mentioned.

The compound (III) or a salt thereof can be produced by the per se known processes and processes analogous thereto. For example, the processes described in Chem. Pharm. Bull. 34, 3747–3761 (1986), and EP-A-0, 378,207 among others, can be utilized.

The salt of compound (II) or of compound (III) includes salts with inorganic acids (e.g. hydrochloric acid, phosphoric acid, hydrobromic acid, surfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid). Where the compound (II) or compound (III) has an acidic group such as —COOH, it can form salts with inorganic bases (alkali metals or alkaline earth metals, e.g. sodium, potassium, calcium, magnesium, ammonium) or salts with organic bases (e.g. tri-$C_{1-3}$ alkylamines such as triethylamine).

The reaction of compound (III) or a salt thereof with compound (II) or a salt thereof can be carried out by causing said compound (III) or salt and said compound (II) or salt to interact in the absence of a solvent or, if necessary, in a solvent. The solvent can be any solvent for chemical reaction unless it does interfere with the intended reaction and, thus, includes various organic solvents such as hydrocarbons (e.g. pentane, hexane, benzene, toluene, nitrobenzene), halogenated hydrocarbons (e.g. dichloromethane, chloroform, 1,2-dichloroethane, carbon tetrachloride), ethers (e.g. ethyl ether, tetrahydrofuran, dioxane, dimethoxyethane), nitroalkanes (e.g. nitromethane, propionitrile), carbon disulfide and so on. Particularly preferred are dichloromethane, 1,2-dichloroethane, nitrobenzene and carbon disulfide. The amount of the solvent is generally 0.5–100 ml and preferably 5–20 ml per millimole of compound (III) or a salt thereof. The reaction temperature is generally about –30° C. through 150° C. and preferably about 20° C. through 100° C. The reaction time is generally 0.5–72 hours and preferably about 1–16 hours.

This reaction can be carried out using a Lewis acid for promotion of the reaction. The Lewis acid includes aluminum chloride, aluminum bromide, zinc chloride, titanium chloride, tin (IV) chloride, boron trifluoride, iron (II) chloride, iron (III) chloride, antimony (V) pentachloride, bismuth (III) chloride, mercury (II) chloride, hydrogen fluoride, sulfuric acid, polyphosphoric acid and so on. Particularly preferred is aluminum chloride. The proportion of the Lewis acid based on each mole of compound (III) or a salt thereof is generally 1–10 moles and preferably 2–10 moles. The amount of compound (II) or a salt thereof per mole of compound (III) or a salt thereof is generally about 1–20 moles and preferably about 1–5 moles.

In the above reaction, the group $$-\overset{O}{\underset{\|}{C}}-(CH)_n-Y$$
$$\phantom{-C-}\overset{|}{R^1}\phantom{-(CH)_n-Y}$$

of said compound (III) or a salt thereof may be introduced into any substitutable position of the ring A of said compound (II) or salt but in the case where the skeletal structure of said compound (II) or salt is 7,11b,12,13-tetrahydro-5H-isoindolo[2,1-b][2]benzazepin-7-one, the above group is predominantly introduced into the 3-position. However, compounds with said group introduced in other positions (1-, 2-and/or 4-position) are also formed and can be fractionated.

The compound of the formula $$Ar-\overset{O}{\underset{\|}{C}}-(CH)_n-N\underset{R^3}{\overset{R^2}{\diagup}}\diagdown \qquad (VI)$$
$$\phantom{Ar-C-}\overset{|}{R^1}\phantom{-(CH)_n-N}$$

wherein all symbols have the same meanings as defined hereinbefore, or a salt thereof can be produced by reacting a compound of the formula $$Ar-\overset{O}{\underset{\|}{C}}-(CH)_n-Z^2 \qquad (IV)$$
$$\phantom{Ar-C-}\overset{|}{R^1}\phantom{-(CH)_n-Z^2}$$

wherein all symbols have the same meanings as defined hereinbefore, or a salt thereof with a compound of the formula $$Z^3-N\underset{R^3}{\overset{R^2}{\diagup}}\diagdown \qquad (V)$$

wherein all symbols have the same meanings as defined hereinbefore, or a salt thereof.

$Z^2$ and $Z^3$ represent groups which react with each other and leave together.

The leaving group $Z^2$ includes halogen (e.g. chloro, bromo, iodo), $C_{1-6}$ alkylsulfonyloxy (e.g. methanesulfonyloxy, ethanesulfonyloxy), $C_{6-10}$ arylsulfonyloxy (e.g. benzenesulfonyloxy, p-toluenesulfonyloxy) and so on. Particularly preferred is halogen. More specifically, such species of halogen as chloro, bromo, etc. are preferred.

The leaving group $Z^3$ which leaves together with $Z^2$ includes hydrogen, trialkylsilyl (e.g. trimethylsilyl, triethylsilyl, t-butyldimethylsilyl) and metal atoms (e.g. sodium, potassium, lithium). Particularly useful is hydrogen.

The hydrocarbon group which may be substituted or the acyl group which may be substituted, as represented by $R^2$ and $R^3$, include those hydrocarbon groups which may be substituted and acyl groups which may be substituted as previously mentioned for $R^{2'}$ and $R^{3'}$.

The nitrogen-containing saturated heterocyclic group which may be substituted wherein $R^2$ and $R^3$ are combined together with the adjacent nitrogen atom is a group bonding through the ring-constituent nitrogen atom among the nitrogen-containing saturated heterocyclic groups which may be substituted as previously mentioned for Y. For example, it may be a group described for ($Y^1$).

The salt of compound (VI) may be similar to the salt of compound (I).

The salt of compound (IV) and of compound (V) includes salts with inorganic acids (e.g. hydrochloric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzensulfonic acid), among others. Furthermore, where the compound (IV) and (V) of this invention have an acidic group such as —COOH, they may form salts with inorganic bases (e.g. alkali metal or alkaline earth metal elements such as sodium, potassium, calcium, magnesium, etc., ammonium) or salts with organic bases (e.g. tri($C_{1-3}$)alkylamines such as triethylamine).

The amount of compound (V) or a salt thereof for use in this reaction is generally 1.0–50.0 molar equivalents, preferably 1.0–10.0 molar equivalents, based on each mole of compound (IV) or a salt thereof. This reaction can be carried out under cooling through heating (0° C.–120° C.). The reaction time is generally 10 minutes—48 hours and preferably 2–16 hours.

While this reaction can be carried out in the absence of a solvent, it can be conduced in a solvent where necessary. The solvent that can be used for this purpose includes any solvents that do not hinder the progress of the reaction, thus including lower alcohols such as methanol, ethanol, propanol, isopropyl alcohol, n-butanol, t-butanol, etc., halogenated hydrocarbons such as dichloromethane, 1,2-dichloroethane, etc., ethers such as dioxane, diethyl ether, tetrahydrofuran, etc., aromatic hydrocarbons such as toluene, benzene, xylene, etc., amides such as dimethylformamide, dimethylacetamide, hexamethylphosphonotriamide, etc., and esters such as ethyl acetate, butyl acetate, etc., among others. The proportion of the solvent based on each millimole of compound (IV-a) or a salt thereof is generally 0.5–100 ml and preferably 5–20 ml.

Where necessary this reaction can be carried out in the presence of a base. The base that can be used includes inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine and so on. The amount of the base with respect to compound (V) or a salt thereof is generally equimolar to a stoichiometric excess and preferably 1.0–5.0 molar equivalents.

To accelerate its progress, this reaction can be carried out in the presence of an iodide (e.g. sodium iodide, potassium iodide, lithium iodide) or the like. The amount of the iodide with respect to compound (IV) or a salt thereof is generally 1–5 molar equivalents and preferably 1.0–1.5 equivalents.

The starting compound (IV) or a salt thereof can be produced by, for example, reacting a compound of the formula

$$Ar—H \qquad (II)$$

wherein Ar has the same meaning as defined hereinbefore, or a salt thereof with a compound of the formula

$$Z^4-\overset{O}{\underset{\|}{C}}-\overset{R^1}{\underset{|}{(CH)_n}}-Z^2 \qquad (VIII)$$

wherein $Z^4$ represents a leaving group; the other symbols have the same meanings as defined hereinbefore.

The leaving group $Z^4$ includes halogen (e.g. chloro, bromo, iodo), $C_{1-6}$ alkylsulfonyloxy (e.g. methanesulfonyloxy, ethanesulfonyloxy), $C_{6-10}$ arylsulfonyloxy (e.g. benzenesulfonyloxy, p-toluene-sulfonyloxy) and so on. Particularly preferred is halogen (e.g. chloro).

The compound (VIII) can be produced by the per se known processes or any processes analogous thereto.

The reaction of compound (II) or a salt thereof with compound (III) can be carried out under the same conditions as the reaction of compound (II) or a salt thereof with compound (III) or a salt thereof.

In the above reaction, the group

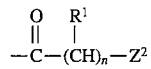

of compound (VIII) can be introduced into any substitutable positions of the ring A of compound (II) or a salt thereof but where the skeletal structure of said compound (II) or a salt thereof is 7,11b,12,13-tetrahydro-5H-isoindolo[2,1-b][2]benzazepin-7-one, the group is predominantly introduced into the 3-position. However, compounds with said group introduced into other positions (1-, 2- and/or 4-position) are also formed and can be fractionated.

The compound (IV) or a salt thereof thus produced can be isolated and purified by the conventional procedures such as concentration, pH adjustment, redistribution, solvent extraction, fractional distillation, distillation, crystallization, recrystallization, chromatography, etc. but the reaction mixture may be submitted to the next reaction without isolation of the compound or a salt thereof.

The starting compound (V) or a salt thereof can be produced by the per se known processes or any processes analogous thereto.

Among species of compound (I), a compound wherein n is equal to 2, that is to say a compound of the formula

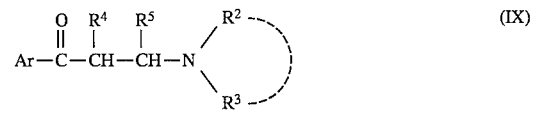

(IX)

wherein $R^4$ and $R^5$ are the same or different and each represents a hydrogen atom or a hydrocarbon group which may be substituted; the other symbols have the same meanings as defined hereinbefore, or a salt thereof can also be produced by, for example, reacting a compound of the formula $$Ar-\overset{O}{\underset{\|}{C}}-CH_2-R^4 \qquad (X)$$

wherein all symbols have the same meanings as defined hereinbefore, or a salt thereof with a compound of the formula $$R^5-CHO \qquad (XI)$$

wherein $R^5$ has the same meaning as defined hereinbefore and a compound of the formula

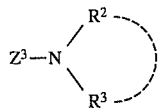
$$(V)$$

wherein all symbols have the same meanings as defined hereinbefore or a salt thereof.

The hydrocarbon group which may be substituted as represented by $R^4$ and $R^5$ includes the hydrocarbon groups which may be substituted as previously mentioned for $R^1$, among others.

The salt of compound (IX) may be similar to the salt of compound (I).

The salt of compound (X) includes salts with inorganic acids (e.g. hydrochloric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid), among others. Furthermore, where compound (X) has an acidic group such as —COOH, the compound (X) may form salts with inorganic bases (e.g. alkali metal or alkaline earth metal elements such as sodium, potassium, calcium, magnesium, etc., ammonium) or salts with organic bases (e.g. tri($C_{1-3}$)alkylamines such as triethylamine).

This reaction can be carried out in the manner of Mannich reaction as described in Organic Reactions Vol. 1, p. 303–341 and other literature. Thus, for example, compound (IX) or a salt thereof can be produced by using generally 0.9–10 equivalents, preferably 1.0–3.0 equivalents, of compound (XI) and compound (V) or a salt thereof with respect to each mole of compound (X) or a salt thereof. This reaction can be conducted generally at ambient temperature or under heating (10°–150° C.) and preferably at a temperature of 80°–120° C. The reaction time is generally 1–48 hours and preferably 2–24 hours. This reaction is generally conducted in the absence of a solvent but can be conducted in a solvent. The solvent that can be used includes any and all solvents that can be used generally in Mannich reaction unless they do not interfere with progress of the reaction and includes alcoholic solvents such as ethanol. The proportion of the solvent with respect to each millimole of compound (X) or a salt thereof is generally 0.5–200 ml and preferably 5–40 ml. If desired, this reaction can be conducted in the presence of an inorganic acid such as hydrochloric acid. The amount of the acid is a catalytic amount with respect to compound (IV) or a salt thereof [0.001–0.05 equivalent per equivalent of compound (X)]. However, when the reactant compound (V) or (X) is not a salt, it is preferable to employ the acid in an additional amount necessary for the formation of a salt.

The compound (X) or a salt thereof can be produced by reacting compound (II) or a salt thereof with a compound of the formula $$Z^5-CO-CH_2-R^4 \qquad (XII)$$

wherein $Z^5$ represents a leaving group; $R^4$ has the same meaning as defined hereinbefore. This reaction can be carried out under the same conditions as the above-mentioned reaction between compound (II) or a salt thereof and compound (VIII).

The compound (XI) can be produced by the per se known processes or any processes analogous thereto.

In the above respective reactions, where the starting compound has an amino, carboxyl or hydroxyl group as a substituent, it may be protected with a protective group which is generally utilized in peptide chemistry, for instance, and the object compound can be obtained on elimination of such protective group after the reaction.

The protective group for the amino function includes optionally substituted $C_{1-6}$ alkyl-carbonyl (e.g. formyl, acetyl, ethylcarbonyl, etc.), benzoyl, $C_{1-6}$ alkyl-oxycarbonyl (e.g. methoxycarbonyl, ethoxycarbonyl), phenyloxycarbonyl (e.g. phenoxycarbonyl), $C_{7-15}$ aralkyl-oxycarbonyl (e.g. benzyloxycarbonyl, fluorenyloxycarbonyl), trityl, phthaloyl and so on. The substituent group that may be present on these groups includes halogen (e.g. fluoro, chloro, bromo, iodo), $C_{1-6}$ alkyl-carbonyl (e.g. methylcarbonyl, ethylcarbonyl, butylcarbonyl), nitro and so on. The number of substituents may range from 1 to about 3. The protective group that can be used for the carboxyl function includes optionally substituted $C_{1-6}$ alkyl (e.g. methyl, ethyl, n-propyl, i-propyl, n-butyl, tert-butyl), phenyl, trityl, silyl and so on. The substituent group that may be present on these groups includes halogen (e.g. fluoro, chloro, bromo, iodo), $C_{1-6}$ alkyl-carbonyl (e.g. formyl, methylcarbonyl, ethylcarbonyl, butylcarbonyl), nitro and on on. The number of such substituent groups may range from 1 to about 3.

The protective group that can be used for the hydroxyl function includes optionally substituted $C_{1-6}$ alkyl (e.g. methyl, ethyl, n-propyl, i-propyl, n-butyl, tert-butyl), phenyl, $C_{7-10}$ aralkyl (e.g. benzyl), $C_{1-6}$ alkyl-carbonyl (e.g. formyl, acetyl, ethylcarbonyl), phenyloxycarbonyl (e.g. phenoxycarbonyl), $C_{7-10}$ aralkylcarbonyl (e.g. benzyloxycarbonyl), pyranyl, furanyl, silyl and so on. The substituent group that may be present includes halogen (e.g. fluoro, chloro, bromo, iodo), $C_{1-6}$ alkyl, phenyl, $C_{7-10}$ aralkyl, nitro and so on. The number of substituents may range from 1 to about 4.

The method of deprotection may be any per se known procedure or any procedure analogous thereto. For example, treatment with an acid or a base, reduction, irradiation with ultraviolet light, and treatment with hydrazine, phenylhydrazine, sodium N-methyldithiocarbamate, tetrabutylammonium fluoride, palladium acetate or the like can be mentioned.

Where the resulting compound (I), (VI) or (IX), inclusive of a salt thereof, has an acylamino group which may be substituted, it can be subjected to deacylation reaction to provide the corresponding compound or salt having a primary or secondary amino group. The starting compound (I), (VI) or (IX), inclusive of a salt thereof, which has an optionally substituted acylamino group, may be isolated and purified by known procedures such as concentration, pH adjustment, redistribution, solvent extraction, fractional distillation, distillation, crystallization, recrystallization, chromatography, etc. but the reaction mixture containing said starting compound or salt may be utilized as the reactant. Thus, the compound (I), (VI) or (IX) having an optionally substituted acylamino group, or a salt thereof, can be deacylated by maintaining the same in an aqueous solution of an acid, e.g. a mineral acid (such as nitric acid, hydrochloric acid, hydrobromic acid, iodic acid, sulfuric acid), or an aqueous solution of a base such as an alkali metal hydroxide (e.g. sodium hydroxide, potassium hydroxide, barium hydroxide, lithium hydroxide) generally at 10°–150° C. or preferably at 50°–100° C. The amount of said acid or base with respect to compound (XII) or a salt thereof is generally 1–100 equivalents and preferably 1–40 equivalents. The strength of the acid or base is generally about 0.1–10 normal and preferably 2–10 normal. The reaction time, which is dependent on the reaction temperature, is generally about 1–24 hours and preferably about 2–10 hours.

The resulting compound (I), (VI) or (IX) having a primary or secondary amino group, or a salt thereof, can be converted to the compound (I), (VI) or (IX), or a salt thereof, whose amino function has been substituted by an optionally substituted hydrocarbon group by introducing the corresponding optionally substituted hydrocarbon group into said primary or secondary amino function. The starting compound (I), (VI) or (IX) having a primary or secondary amino group, or a salt thereof, can be put to use after isolation and purification by the conventional procedure such as concentration, pH adjustment, redistribution, solvent extraction, fractional distillation, distillation, crystallization, recrystallization, chromatography, etc. but the reaction mixture containing the same can be diretly used as the starting material. Thus, the compound (I), (VI) or (IX), or a salt thereof, whose amino function has been substituted by an optionally substituted hydrocarbon residue can also be produced by reacting said compound (I), (VI) or (IX) having a primary or secondary amino group, or a salt thereof, with a compound of the formula $$R^7—Z^{3'} \quad (XIII)$$

wherein $R^7$ represents a hydrocarbon residue which may be substituted; $Z^{3'}$ represents a leaving group.

The optionally substituted hydrocarbon group $R^7$ may be any of the hydrocarbon groups which may be substituted as mentioned previously for $R^2$, $R^3$ and $R^6$.

The leaving group $Z^{3'}$ includes halogen (e.g. chloro, bromo, iodo), $C^{1-6}$ alkylsulfonyloxy (e.g. methanesulfonyloxy, ethanesulfonyloxy) and $C_{6-10}$ arylsulfonyloxy (e.g. benzenesulfonyloxy, p-toluenesulfonyloxy), among others. Particularly preferred is a halogen atom (e.g. chlorine).

The above reaction can be carried out in the absence of a solvent or in a solvent, and where necessary in the presence of a base. The base mentioned just above includes inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine and so on. Where a solvent is employed, the solvent should be selected from among those which do not interfere with the reaction, namely lower alcohols such as methanol, ethanol, propanol, isopropyl alcohol, n-butanol, t-butanol, etc., halogenated hydrocarbons such as dichloromethane, 1,2-dichloroethane, etc., ethers such as dioxane, diethyl ether, tetrahydrofuran, etc., aromatic hydrocarbons such as toluene, benzene, xylene, etc., amides such as dimethylformamide, dimethylacetemide, hexamethylphosphonotriamide, etc. and esters such as ethyl acetate, butyl acetate, etc., among other solvents. This reaction can be carried out under cooling (about 0° C.–10° C.), at ambient temperature (about 10° C.–40° C.) or under heating (about 40° C.–120° C.) and the reaction time is generally 10 minutes—48 hours and preferably about 2–16 hours. The preferred amount of compound (XIII) with respect to the compound (I), (VI) or (IX) having a primary or secondary amino group, or a salt thereof, is generally 0.3–5.0 molar equivalents. The amount of the base, when used, is generally equimolar to a stoichiometric excess and preferably 1.1–5 molar equivalents with respect to the compound (I), (VI) or (IX) having a primary or secondary amino group or a salt thereof.

If desired, this reaction can be hastened by conducting it in the presence of an iodide such as sodium iodide, potassium iodide or lithium iodide. When the reaction is carried out in the presence of such an iodide, the amount of the iodide is generally 1–5 molar equivalents and preferably 1.1–1.5 molar equivalents with respect to compound (XI).

The compound (XIII) can be produced by per se known processes or any processes analogous thereto.

When the compound (I) thus obtained is a free compound, it can be converted to a salt by the conventional procedure, while any salt thereof can be converted to the free compound or a different kind of salt by the procedure respectively known per se. The compound (I) or its salt thus obtained can be isolated and purified by the known procedures mentioned hereinbefore. While the compound (I) or its salt includes stereoisomers due to the presence of asymmetric carbon, these can also be isolated and purified by a choice of the above-mentioned known procedures, fractional recrystallization, chromatography on an optically active column, and other procedures.

The compound (I) and a salt thereof of this invention act on the central nervous system of mammalian animals and, having strong cholinesterase inhibitory activity, display excellent anti-amnesia activity against various amnestic factors in man and animals (e.g. mouse).

Furthermore, the compound (I) and salt thereof have monoamine (e.g. norepinephrine and serotonin)-reuptake inhibitory activity and exhibits excellent antidepressant effects in man and animals (e.g. mouse).

The compound (I), inclusive of its salt, is remarkably superior to physostigmine and THA in the isolation of central nervous system effect vs. peripheral nervous system effect and in doses producing antiamnesic and antidepressive effects, it causes no or little peripheral nervous symptoms such as convulsion, sialism and diarrhea, features a long duration of action and has a low toxic potential. It also exhibits remarkable efficacy on oral administration. The acute toxicity ($LD_{50}$) of the compound (I) or a salt thereof of this invention is not less than 100 mg/kg.

Therefore, the substance according to this invention is of value as a safe brain function-improving agent for man and other mammalian animals.

The disease in which the substance of this invention can be indicated with therapeutic success includes senile dementia, Altzheimer's disease, Huntigton's cholea, hyperkinesia and maniac and, therefore, the substance of this invention finds application in the prevention and treatment of these diseases.

The substance of this invention can be administered orally or otherwise, generally in admixture with a medicinally acceptable carrier or excepient, to mammals inclusive of man.

Such formulations may be provided in oral dosage forms (e.g. powders, tablets, granules, capsules) or parenteral dosage forms (e.g. suppositories, injections).

These dosage forms can be manufactured by the per se known methods. The dosage depends on the type and symptoms of the disease to be managed but generally speaking, about 0.01 mg–50 mg, preferably 0.1–30 mg, and more desirably 0.5–10 mg can be dispensed per day in the case of an adult (body weight: 70 kg).

EXAMPLES

The following examples, reference examples, formulation examples and test examples are all intended to illustrate this invention in further detail and should by no means be construed as defining the scope of the invention.

Unless otherwise indicated, all elution procedures in column chromatography as described in the test and reference examples were carried out under TLC (thin-layer chromatography) monitoring. In the TLC monitoring, Merck 60$F_{254}$ was used as the TLC plate, the eluent for column chromatography was used as the TLC developer, and a UV detector was used for detection. In addition, the TLC plate was sprayed with 48% HBr, heated for hydrolysis, sprayed with ninhydrin reagent and reheated to see that the spot would turn red-red-purple. The fractions thus comfirmed to contain the object compound were pooled. Unless otherwise indicated, the column packing silica gel used was Merck's Kieselgel 60 (70–230 mesh).

The term "atmospheric temperature" or "ambient temperature" as used herein generally means any temperature between about 5° C. and about 40° C., while the term "atmospheric pressure" means any pressure in the neighborhood of 1 atm.

Unless otherwise indicated, % means a weight percentage and $C_4H_4O_4$ stands for fumaric acid.

Reference Example 1

7,11b,12,13-tetrahydro-5H-isoindro[2,1-b][2]benzazepin-7-one

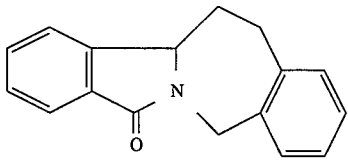

A mixture of 9.8 g 11b,12-dihydro-5H-isoindolo-[2,1-b][2,1-b]benzazepine-7,13-dione, 5.0 g potassium hydroxide, 4.3 ml hydrazine monohydrate and 50 ml ethylene glycol was heated at 120° C. for 2 hours and, then, at 190° C. for 3 hours. The reaction mixture was allowed to cool, after which it was diluted with water and extracted with dichloromethane. The extract was dried over anhydrous sodium sulfate and the solvent was distilled off under reduced pressure. The residue was purified by silica gel column chromatography (eluent: dichloromethane-ethyl acetate= 20:1 (v/v)) and the crystals obtained were recrystallized from ethyl acetate-ether to provide 4.2 g of the title compound as light-yellow needles melting at 170°–171° C. Elemental analysis for $C_{17}H_{15}NO$ Calcd.: C, 81.90; H, 6.06; N, 5.62

Found: C, 81.76; H, 6.02; N, 5.48

Reference Example 2

5,5a-Dihydroindolo[2,1-b][3]benzazepine-6,12(11H)-dione

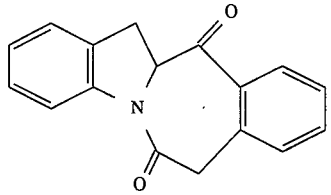

1) In a mixture of 360 ml THF and 360 ml 1N-aqueous sodium hydroxide solution was dissolved 32 g of methyl 2,3-dihydro-1H-indole-2-carboxylate, followed by dropwise addition of 25.1 ml of phenylacetyl chloride at 0° C. The resulting mixture was stirred at ambient temperature for 2 hours and the THF was distilled off under reduced pressure. This aqueous solution was washed with 200 ml of ether twice, adjusted to pH 3–4 with concentrated hydrochloric acid, and extracted with 500 ml of dichloromethane-methanol (4:1) twice. The extract was dried over anhydrous sodium sulfate and the solvent was distilled of under reduced pressure. The solid residue was suspended in 200 ml of ether and the resulting crystals were collected by filtration to provide 36.0 g of 1-phenylacetyl-2,3-dihydro-1H-indole-2-carboxylic acid as crystals melting at 191°–192° C. Elemental analysis for $C_{17}H_{15}NO_3$ Calcd.: C, 72.58; H, 5.37; N, 4.98

Found : C, 72.46; H, 5.44; N, 4.86

2) 14.8 g of the 1-phenylacetyl-2,3-dihydro-1H-indole-2-carboxylic acid obtained in 1) above was suspended in 150 ml of dichloromethane followed by addition of 4 ml of thionyl chloride. The mixture was stirred in an ambient atmosphere for 16 hours, at the end of which time it was cooled to 0° C. To this mixture was added 20 g of anhydrous aluminum chloride with caution to prevent the temperature of the reaction system from rising beyond 5° C. The mixture was further stirred at the same temperature for 2 hours and, then, poured in 30 ml of iced water. This mixture was extracted with 200 ml of dichloromethane twice. The extract was washed with 300 ml of 1N-aqueous sodium hydroxide solution and dried over anhydrous sodium sulfate. The solvent was then distilled off and the residue was crystallized from ether to provide 4.4 g of the title compound as colorless crystals melting at 224°–226° C. Elemental analysis for $C_{17}H_{13}NO_2$ Calcd.: C, 77.55; H, 4.98; N, 5.32

Found : C, 77.49; H, 4.98; N, 5.11

Reference Example 3

2,3,6b,7,8,9,10,10a-Octahydro-1H-pyrido[3,2,1-jk]carbazol-6-one

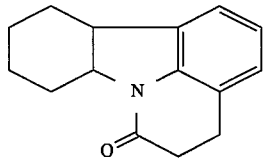

1) To a solution of 10 g 1,2,3,4,4a,9a-hexahydrocarbazole in 30 ml acetone was added a solution of 8.3 g 3-chloropropionyl chloride in 30 ml acetone dropwise at ambient temperature and the mixture was refluxed for 1 hour. The solvent was then distilled off under reduced pressure and the residue was dissolved in 100 ml of dichloromethane and washed with 10% hydrochloric acid twice. The solution was dried over anhydrous sodium sulfate and the solvent was distilled off under reduced pressure to provide about 17 g of 9-(3-chloropropionyl)-1,2,3,4,4a,9a-hexahydrocarbazole as a viscous oil. This oil was not purified but submitted directly to the next reaction.

2) The 9-(3-chloropropionyl)-1,2,3,4,4a,9a-hexahydrocarbazole (3.0 g) obtained as above was mixed with 3.3 g of anhydrous aluminum chloride and the mixture was heated at 120° C. with stirring for 90 minutes. This mixture was diluted with iced water and extracted with dichloromethane. The extract was then washed with water and dried over anhydrous sodium sulfate and the solvent was distilled off. The residue was purified by silica gel column chromatography (eluent: ethyl acetate-dichloromethane=1:1, v/v) to provide 1.7 g of the title compound as colorless crystals melting at 66°–70° C. Elemental analysis for $C_{15}H_{17}NO$ Calcd.: C, 79.26; H, 7.54; N, 6.16

Found : C, 79.19; H, 7.52; N, 6.11

Reference Example 4

5-(3-Chloro-1-oxopropyl)-2,3,6b,7,8,9,10,10a-octahydro-1H-pyrido[3,2,1-jk]carbazol-6-one

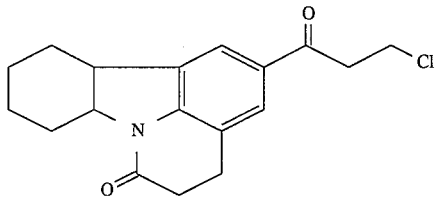

To a solution of 0.52 g 2,3,6b,7,8,9,10,10a-octahydro-1H-pyrido[3,2,1-jk]carbazol-6-one obtained in Reference Example 3 and 0.32 g 3-chloropropionyl chloride in 20 ml 1,2-dichloroethane was added 0.70 g of anhydrous aluminum chloride portionwise and the mixture was refluxed for 1 hour. The reaction mixture was allowed to cool, poured in iced water and extracted with dichloromethane. The extract was washed with water and dried over anhydrous sodium sulfate and the solvent was distilled off under reduced pressure. The residue was purified by silica gel column chromatography (eluent: ethyl acetate-dichloromethane= 1:1, v/v) to provide 0.50 g of the title compound as colorless crystals melting at 126°–128° C. Elemental analysis for $C_{18}H_{20}ClNO_2$ Calcd.: C, 68.03; H, 6.34; N, 4.41

Found : C, 67.81; H, 6.37; N, 4.39

Reference Example 5

Using the compound obtained in Reference Example 1 or a known tetracyclic fused ring and 3-chloropropionyl chloride, the procedure of Reference Example 4 was otherwise repeated to provide the compounds shown in Table 13.

TABLE 13

$$Ar-\overset{O}{\underset{\|}{C}}-CH_2CH_2Cl$$

| Compound No. | Ar | Melting Point (°C.) | Molecular formula | Elemental analysis Calcd. (Found) | | |
|---|---|---|---|---|---|---|
| | | | | C | H | N |
| 1 | | 139–142 | $C_{20}H_{18}ClNO_2$ | 70.69 (70.72 | 5.34 5.39 | 4.12 4.10) |
| 2 | | 152–156 | $C_{20}H_{18}ClNO_2$ | 70.69 (70.61 | 5.34 5.39 | 4.12 4.13) |

TABLE 13-continued $$Ar-\overset{\overset{O}{\|}}{C}-CH_2CH_2Cl$$

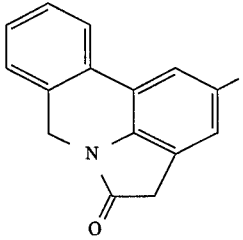

| Compound No. | Ar | Melting Point (°C.) | Molecular formula | Elemental analysis Calcd. (Found) | | |
|---|---|---|---|---|---|---|
| | | | | C | H | N |
| 3 | | 92–95 | $C_{18}H_{14}NO_2Cl$ | 69.35 (69.11 | 4.53 4.75 | 4.49 4.27) |

Reference Example 6

3-[1-[(4-Nitrophenyl)methoxycarbonyl]-4-piperidinyl]propionic acid

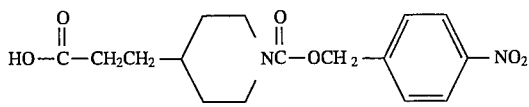

A mixture of 20.0 g 3-(1-acetyl-4-piperidinyl)propionic acid and 40 ml concentrated hydrochloric acid was refluxed for 14 hours. The hydrochloric acid was then distilled off under reduced pressure and the residual powder was washed with ether and dried under reduced pressure to provide 19.0 g of a colorless powder. To a solution of this powder in 170 ml 1N-sodium hydroxide solution was added a solution of 12.2 g p-nitrobenzyl chloroformate in 60 ml dichloromethane with ice cooling and the mixture was then stirred vigorously at ambient temperature for 1 hour. The organic layer was separated from this reaction mixture and the aqueous layer was acidified with 3N-hydrochloric acid and extracted with dichloromethane. The extract was dried over anhydrous sodium sulfate and the solvent was distilled off under reduced pressure. The residue was dissolved in dichloromethane with heating and ether was then added. The mixture was allowed to cool and the resulting powder was collected by filtration and dried under reduced pressure to provide 16.6 g of the title compound as a colorless powder melting at 98°–99° C. Elemental analysis for $C_{16}H_{20}N_2O_6$ Calcd.: C, 57.14; H, 5.99; N, 8.33

Found : C, 57.05; H, 6.01; N, 8.28

Reference Example 7

4,5-Dihydro-7H-pyrrolo[3,2,1-de]phenanthridin-4-one a) 5-(Chloroacetyl)-4,5-dihydrophenanthridine A solution of chloroacetyl chloride (17 g) in dichloromethane (20 ml) was added dropwise to a mixture of 5,6-dihydrophenanthridine (25 g) in dichloromethane (80 ml) and 1N-NaOH with vigorous stirring at 0° C. The mixture was allowed to warm to room temperature and stirring was continued for an hour. An organic phase was separated, washed with sat. $NaHCO_3$ twice, dried over $Na_2SO_4$ and concentrated in vacuo. The resulting solid was recrystallized from ethyl acetate-hexane to give 33 g of the title compound as colorless needles, mp 115°–117° C. Anal. Calcd for $C_{15}H_{12}NOCi$: C, 69.91; H, 4.69; N, 5.43. Found: C, 69.85; H, 4.41; N, 5.33.

b) 4,5-Dihydro-7H-pyrrolo[3,2,1-de]phenanthridin-4-one

A mixture of 5-(chloroacetyl)-4,5-dihydrophenanthridine (30 g) and aluminum chloride (36 g) was warmed up to 140° C. and stirred for 10 minutes. Water was added to the mixture and extracted with dichloromethane. The extracts were washed with water, dried over $Na_2SO_4$ and concentrated in vacuo. The resulting solid was recrystallized from dichloromethane-ether to give 18 g of the title compound as colorless needles, mp 199°–202° C. Anal. Calcd for $C_{15}H_{11}NO$: C, 81.43; H, 5.01; N, 6.33. Found: C, 81.16; H, 5.18; N, 6.29.

EXAMPLE 1

5-[3-[4-(Phenylmethyl)-1-piperazinyl]-1-oxopropyl]-2,3,6b,7,8,9,10,10a-octahydro-1H-pyrido[3,2,1-jk]carbazol-6-one dihydrochloride

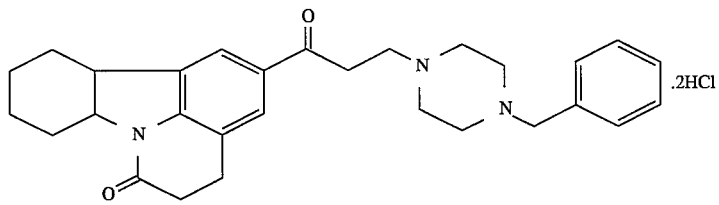

A mixture of 0.40 g 5-(3-chloro-1-oxopropyl)-2,3,6b,7,8,9,10,10a-octahydro-1H-pyrido[3,2,1-jk]-carbazol-6-one as obtained in Reference Example 4, 0.23 g potassium carbonate, 0.29 g 1-benzylpiperazine and 20 ml dichloromethane-methanol (1:1, v/v) was stirred at ambient temperature for 14 hours and the solvent was then distilled off under reduced pressure. The residue was diluted with water and extracted with dichloromethane. The extract was washed with water, dried over anhydrous sodium sulfate and the solvent was distilled off. The risidue was purified by silica gel column chromatography (eluent: ethyl acetate-methanol=4:1, v/v) to provide 0.61 g of the free base form of the title compound as oil. This oil was dissolved in methanol followed by addition of 0.8 ml of 4N-methanolic HCl. The resulting crystals were collected by filtration, washed with ether and dried under reduced pressure to provide 0.59 g of the title compound as colorless crystals melting at 199°–203° C. (decomp.). Elemental analysis for $C_{29}H_{35}N_3O_2 \cdot 2HCl \cdot H_2O$ Calcd.: C, 63.50; H, 7.17; N, 7.66

Found : C, 63.22; H, 7.10; N, 7.73

EXAMPLE 2

Using the compound obtained in Reference Example 5, the procedure of Example 1 was otherwise repeated to provide the compounds shown in Table 14.

TABLE 14

$$Ar-\underset{\underset{O}{\|}}{C}-CH_2CH_2-N\diagup\diagdown N-CH_2-\text{(phenyl)}$$

| Compound No. | Ar | Melting Point (°C.) | Molecular formula | Elemental analysis Calcd. (Found) | | |
|---|---|---|---|---|---|---|
| | | | | C | H | N |
| 1 | (structure) | 195–197 | $C_{31}H_{33}N_3O_2 \cdot$ 2HCl.H$_2$O | 65.26 (65.52 | 6.54 6.43 | 7.36 7.30) |
| 2 | (structure) | 147–152 | $C_{31}H_{33}N_3O_2 \cdot$ 2HCl.2H$_2$O | 63.26 (63.47 | 6.68 6.94 | 7.14 6.80) |
| 3 | (structure) | 222–225 (decomposition) | $C_{29}H_{29}N_3O_2 \cdot$ 2HCl.2H$_2$O | 64.21 (64.35 | 6.13 6.08 | 7.75 7.81) |

EXAMPLE 3

3-[3-[1-[(4-Nitrophenyl)methoxycarbony]-4-piperidinyl]-1-oxo-propyl]-7,11b,12,13-tetrahydro-5H-isoindolo[2,1-b][2]benzazepin-7-one

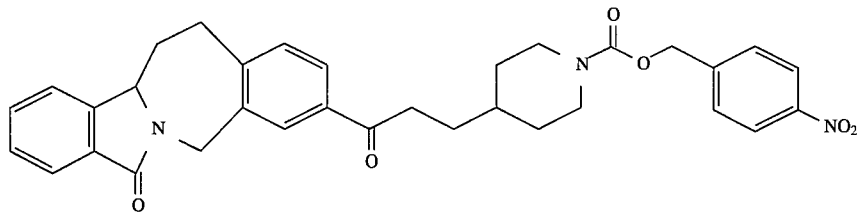

3-[1-[(4-Nitrophenyl)methoxycarbonyl]-4-piperidinyl] propionic acid as obtained in Reference Example 6 (2.45 g) was added to 10 ml of thionyl chloride at 0°–5° C. and the mixture was stirred at 0°–5° C. for 20 minutes. The excess thionyl chloride was then distilled off under reduced pressure. This residue and 1.6 g of the 7,11b,12,13-tetrahydro-5H-isoindolo[2,1-b][2]benzazepin-7-one obtained in Reference Example 1 were dissolved in 30 ml of 1,2-dichloroethane and 3.0 g of anhydrous aluminum chloride was added in small portions to the solution. The mixture was stirred at ambient temperature for 14 hours. The reaction mixture was then poured in iced water and extracted with dichloromethane. The extract was washed with water and dried over anhydrous sodium sulfate and the solvent was distilled off under reduced pressure. The residue was purified by silica gel column chromatography (eluent:dichloromethane-ethyl acetate=20:1, v/v) to provide 0.90 g of the title compound as colorless crystals melting at 179°–181° C. Elemental analysis for $C_{33}H_{33}N_3O_6$ Calcd.: C, 69.83; H, 5.86; N, 7.40

Found: C, 69.69; H, 5.73; N, 7.38

EXAMPLE 4

3-[3-[1-(Phenylmethyl)-4-piperidinyl]-1-oxopropyl]-7,11b,12,13-tetrahydro-5H-isoindolo[2,1-b][2]benzazepin-7-one hydrochloride

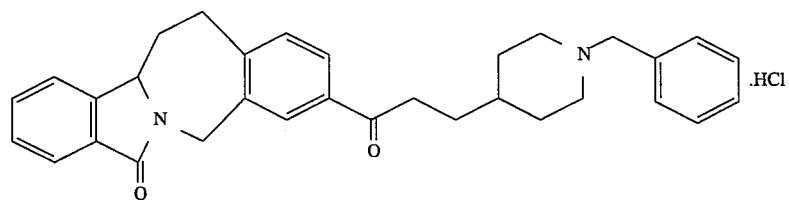

A solution of 0.8 g 3-[3-[1-[(4-nitrophenyl)methoxycarbonyl]-4-piperidinyl]-1-oxopropyl]-7,11b,12t13-tetrahydro-5H-isoindolo[2,1-b][2]-bensasepin-7-one as obtained in Example 3 in 40 ml methanol was mixed with 0.4 ml 4N-methanolic HCl and the mixture was subjected to catalytic hydrogenation reaction in the presence of 10% Pd/C at atmospheric pressure. After completion of the reaction, the 10% Pd/C was filtered off and the filtrate was concentrated. The residue was dissolved in water, adjusted to pH 10–11 with 10% aqueous sodium hydroxide solution and extracted with dichloromethane. The extract was washed with water and dried over anhydrous sodium sulfate and the solvent was distilled off under reduced pressure to recover 0.53 g of oil. To a suspension comprising 0.43 g of this oil, 0.2 g of potassium carbonate and 10 ml of ethanol was added a solution of 0.18 g benzyl bromide in 2 ml ethanol dropwise and the mixture was stirred at ambient temperature for 4 hours. The solvent was then distilled off under reduced pressure and the residue was dissolved in water and extracted with dichloromethane. The extract was washed with water and dried over anhydrous sodium sulfate and the solvent was distilled off under reduced pressure. The residue was purified by silica gel column chromatography (eluent: ethyl acetate-methanol=40:1, v/v) to provide 0.36 g of the free base form of the title compound as a colorless powder melting at 146°–147° C. This powder was dissolved in methanol followed by addition of 0.3 ml of 4N-methanolic HCl. After the solvent was distilled off, isopropyl alcohol was added and the resulting solid was dried under reduced pressure to provide 0.35 g of the title compound as a colorless powder melting at 179°–181° C. Elemental analysis for $C_{32}H_{34}N_2O_2 \cdot HCl \cdot \frac{1}{2}H_2O$ Calcd.: C, 73.34; H, 6.92; N, 5.35

Found : C, 73.56; H, 6.90; N, 5.25

EXAMPLE 5

3-[1-Oxo-3-(1-piperazinyl)propyl]-7,11b,12,13-tetrahydro-5H-isoindolo[2,1-b][2]benzazepin-7-one

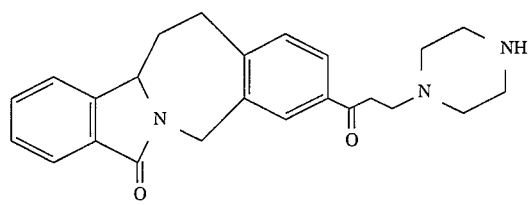

Using 3.45 g of 3-(3-chloro-1-oxopropyl)-7,11b,12,13-tetrahydro-5H-isoindolo[2,1-b][2]benzazepin-7-one, corresponding to Reference Example 5 Compound No. 1, and 1.4 g of 1-formylpiperazine, the procedure of Example 1 was otherwise repeated to provide about 3.6 g of 3-[3-(4-formyl-1-piperazinyl)-1-oxopropyl]-7,11b,12,13-tetrahydro-5H-isoindolo[2,1-b][2]benzazepin-7-one as a crude oil. This oil was not further purified but directly dissolved in 50 ml of methanol and the solution was refluxed with 50 ml of concentrated hydrochloric acid for 4 hours. After the methanol was distilled off, the residual aqueous solution was adjusted to pH about 10 with 10% aqueous sodium hydroxide solution and the product was extracted into dichloromethane. The extract was washed with water and the solvent was distilled off under reduced pressure to provide 3.1 g of the title compound as a powder melting at 207°–210° C. Elemental analysis for $C_{24}H_{27}N_3O_2$ Calcd.: C, 74.01; H, 6.99; N, 10.79

Found : C, 73.92; H, 7.05; N, 11.84

EXAMPLE 6

Using the compound obtained in Example 5 and various kinds of substituted benzyl bromide, the procedure of Example 1 was repeated to provide the compounds shown in Table 15.

TABLE 15

| Compound No. | X | Melting Point (°C.) | Molecular formula | Elemental analysis Calcd. (Found) | | |
|---|---|---|---|---|---|---|
| | | | | C | H | N |
| 1 | 3-CH₃ | 207–211 (decomp.) | $C_{32}H_{35}N_3O_2$·2HCl.½H₂O | 62.84 (62.91 | 6.92 6.98 | 6.87 6.92) |
| 2 | 3-Cl | 206–208 (decomp.) | $C_{31}H_{32}ClN_3O_2$·2HCl.½H₂O | 62.47 (62.54 | 5.92 5.84 | 7.05 6.95) |
| 3 | 3-F | 194–196 (decomp.) | $C_{31}H_{32}FN_3O_2$·2HCl.½H₂O | 64.25 (64.44 | 6.09 5.99 | 7.25 7.01) |
| 4 | 3-CN | 199–202 (decomp.) | $C_{32}H_{32}N_4O_2$·2HCl.½H₂O | 65.53 (65.13 | 6.01 5.76 | 9.55 9.24) |

EXAMPLE 7

5-[3-[1-(Phenylmethyl)-4-piperidinyl]1-oxopropyl]-2,3,6b,7,8,9,10,10a-octahydro-1H-pyrido[3,2,1-jk]carbazol-6-one fumarate

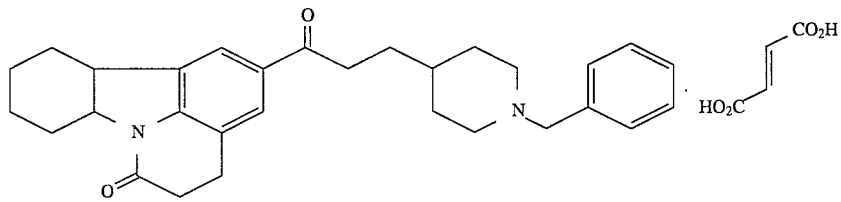

1) One (1.0) gram of 3-(1-methoxycarbonyl-4-piperidinyl)propionic acid was added to 5 ml of thionyl chloride at 0°–5° C. and the mixture was stirred at 0°–5° C. for 20 minutes. The excess thionyl chloride was distilled off under reduced pressure. To a solution of this distillation residue and 1.0 g 2,3,6b,7,8,9,10,10a-octahydro-1H-pyrido[3,2,1-jk]carbazol-6-one as obtained in Reference Example 3 in 50 ml 1,2-dichloroethane was added 2.1 g of anhydrous aluminum chloride portionwise and the mixture was stirred at ambient temperature for 14 hours. The reaction mixture was poured in iced water and extracted with dichloromethane. The extract was washed with 10% aqueous sodium hydroxide solution and water in that order and dried over anhydrous sodium sulfate and the solvent was then distilled off under reduced pressure. The residue was purified by silica gel column chromatography (eluent: dichloromethane-ethyl acetate=10:1, v/v) to provide 0.69 g of 5-[3-[1-(methoxycarbonyl)-4-piperidinyl]-1-oxopropyl]-2,3,6b,7,8,9,10,10a-octahydro-1H-pyrido[3,2,1-jk]carbazol-6-one. In addition, 0.34 g of the starting compound 2,3,6b,7,8,9,10,10a-octahydro-1H-pyrido[3,2,1-jk]carbazol-6-one was recovered.

2) A mixture of 0.38 g of the compound obtained in 1) above and 20 ml of concentrated hydrochloric acid was refluxed for 14 hours. The hydrochloric acid was then distilled off under reduced pressure and the residue was diluted with water and washed with ethyl acetate. This aqueous solution was adjusted to pH about 10 with 10% aqueous sodium hydroxide solution and extracted with dichloromethane. The extract was washed with water and dried over anhydrous sodium sulfate and the solvent was distilled off under reduced pressure. To a suspension comprising 0.27 g of the oily residue, 0.13 g of potassium carbonate and 15 ml of methanol was added a solution of 0.115 g benzyl bromide in 3 ml methanol and the mixture was stirred at ambient temperature for 4 hours. The solvent was then distilled off and the residue was diluted with water and extracted with dichloromethane. This extract was washed with water and dried over anhydrous sodium sulfate and the solvent was distilled off under reduced pressure. The residue was purified by silica gel column chromatography (eluent: ethyl acetate-methanol=10:1, v/v) to provide 0.2 g of the free base form of the title compound as oil. This oil was treated with 1 equivalent of fumaric acid to provide 0.2 g of the title compound as a colorless amorphous powder. Elemental analysis for $C_{30}H_{36}N_2O_2 \cdot C_4H_4O_4 \cdot 2H_2O$ Calcd.: C, 67.09; H, 7.29; N, 4.60

Found : C, 67.29; H, 6.97; N, 4.32

EXAMPLE 8

11-[1-Oxo-3-[4-(phenylmethyl)-1-piperazinyl]]-7,8, 13,13a-tetrahydro-5H-isoindolo[1,2-b][3]benzazepin-5-one dihydrochloride(A) and 10-[1-oxo-3-[4-(phenylmethyl)-1-piperazinyl]]-7,8,13,13a-tetrahydro-5H-isoindolo[1,2-b][3]benzazepin-5-one dihydrochloride(B)

To a solution of 2.49 g 7,8,13,13a-tetrahydro-5H-isoindolo[1,2-b][3]benzazepin-one and 1.05 ml 3-chloropropionyl chloride in 25 ml 1,2-dichloroethane was added 2.93 g of anhydrous aluminum chloride portionwise and the mixture was stirred at ambient temperature for 3 hours. The reaction mixture was poured in iced water and extracted with dichloromethane. This extract was washed with 1N-aqueous sodium hydroxide solution and water in the order mentioned and dried over anhydrous sodium sulfate. The solvent was distilled off under reduced pressure and the residue was purified by silica gel column chromatography (eluent: dichloromethane-ethyl acetate=10:1, v/v) to give 2.46 g of a light-yellow powder. To a suspension comprising 1.70 g of the above powder, 0.69 g of potassium carbonate and 43 ml of ethanol was added 1.04 ml of 1-benzylpiperazine and the mixture was stirred at ambient temperature for 5 hours. The solvent was then distilled off under reduced pressure and the residue was diluted with water and extracted with dichloromethane. This extract was washed with water and dried over anhydrous sodium sulfate and the solvent was distilled off under reduced pressure. The residue was purified by silica gel column chromatography (eluent: ethyl acetate-methanol=10:1, v/v) to provide 2.20 g of the free base forms of the title compound as a colorless powder. This powder (0.96 g) was treated with methanolic hydrochloric acid (2 equivalents) to provide 0.76 g of an approximately 4:1 mixture of the title compounds (A) and (B) as an amorphous powder. Elemental analysis for $C_{31}H_{33}N_3O_2 \cdot 2HCl \cdot \frac{1}{2}H_2O$ Calcd.: C, 66.31; H, 6.46; N, 7.48

Found : C, 66.20; H, 6.52; N, 7.42

Formulation Example 1

| | | |
|---|---|---|
| (1) | 3-[3-[1-(Phenylmethyl)-4-piperidinyl]-1-oxopropyl]-7,11b,12,13-tetrahydro-5H-isoindolo[2,1-b][2]benzazepin-7-one hydrochloride (the compound of Example 4) | 1 g |
| (2) | Lactose | 197 g |
| (3) | Corn starch | 50 g |
| (4) | Magnesium stearate | 2 g |

One gram of (1), 197 g of (2) and 20 g of (3) (corn starch) were blended and granulated together with a paste prepared

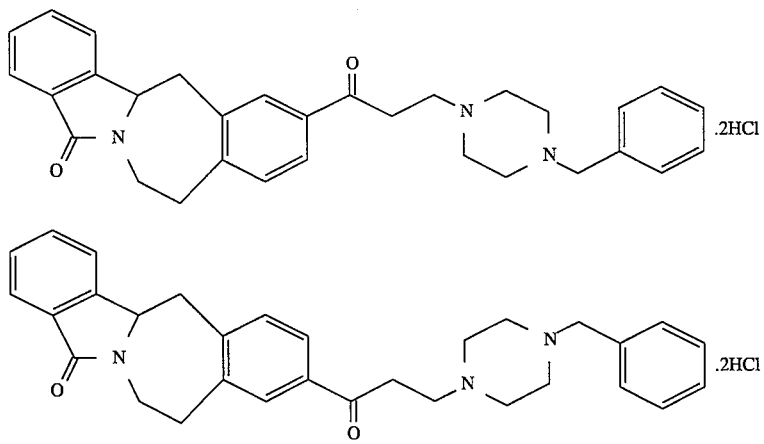

(A)

(B)

from 15 g of corn starch and 25 ml of water. To this granuation was added 15 g of corn starch and 2 g of (4) and the composition was compressed with a tablet machine to manufacture 2000 tablets each containing 0.5 mg of (1) and measuring 3 mm in diameter.

Formulation Example 2

| | | |
|---|---|---|
| (1) | 3-[3-[1-(Phenylmethyl)-4-piperidinyl]-1-oxopropyl]-7,11b,12,13-tetrahydro-5H-isoindolo[2,1-b][2]benzazepin-7-one hydrochloride (the compound of Example 4) | 2 g |
| (2) | Lactose | 197 g |
| (3) | Corn starch | 50 g |
| (4) | Magnesium stearate | 2 g |

Two grams of (1), 197 g of (2) and 20 g of (3) (corn starch) were blended and granulated together with a paste prepared from 15 g of corn starch and 25 ml of water. To this granulation was added 15 g of corn starch and 2 g of (4) and the composition was compressed with a tablet machine to manufacture 2000 tablets each measuring 3 mm in diameter and containing 1.0 mg of (1).

Test Example 1

The cholinesterase inhibitory activity of the compound of this invention was evaluated using (acetyl[[$^3$H])-acetylcholine. Thus, using the $S_1$ fraction of a male Wistar rat cerebral cortex homogenate as a source of cholinesterase, (acetyl[$^3$H])-acetylcholine as a substrate, and the compound of this invention as a test substance, the system was incubated for 30 minutes. The reaction was then stopped and a toluenic scincillator was added. After shaking, [$^3$H]-acetic acid produced and transferred into the toluene layer was counted with a liquid scincillation counter to estimate the cholinesterase inhibitory activity of the test substance.

The cholinesterase inhibitory activity of the test compound was expressed in 50% inhibitory concentration ($IC_{50}$). The cholinesterase inhibitory activity values of physostigmine and THA were also determined in a similar fashion.

The data are presented in Table 16.

TABLE 16

| Compound (Example No.) | Acetylcholinesterase inhibitory activity $IC_{50}$ (µM) |
|---|---|
| 1 | 0.0775 |
| 2-1 | 0.0164 |
| 4 | 0.0024 |
| 6-2 | 0.0655 |
| 6-3 | 0.0174 |
| 7 | 0.00793 |
| 8 | 0.00403 |
| Physostigmine | 0.220 |
| THA | 0.300 |

It is apparent from Table 16 that the compound of this invention is superior to physostigmine and THA in acetylcholinesterase inhibitory activity.

Test Example 2

The monoamine reuptake inhibitory activity of the compound of this invention was evaluated using [$^3$H]-norepinephrine (NE) and [$^3$H]-serotonin(5-HT).

Thus, the brain was enuleated from male JCl: Wistar rats (aged 9–13 weeks) and the cerebral cortex and the hippocampus were isolated. The tissue was homogenized (Potter, 5 strokes) with about 10–15 volumes of ice-cooled 0.32M sucrose and centrifuged at 1.000×g for 10 minutes. The supernatant was further centrifuged at 20,000×g for 20 minutes to provide a pellet ($P_2$). This pellet was suspended in Krebs-Ringer bicarbonate solution (KRB) (KRB: 116 mM NaCl, 4.8 mM KCl, 1.3 mM $CaCl_2$, 1,2 mM $MgSO_4$, 1,2 mM $NaH_2PO_4$, 25 mM $NaHCO_3$, 0.1 mM EDTA-2Na, 11.1 mM D-glucose, 0.11 mM L-ascorbic acid, 0.01 mM pargyline-HCl; 95% $O_2$/5% $CO_2$) and aliquots of the suspension were used for assays.

The test compound (10 µl as dissolved in DMSO at 100 times the final concentration) was mixed with 900 µl of the $P_2$ suspension and the mixture was preincubated at 37° C. for 5 minutes. Then, 100 µl of [$^3$H]-NE (final concentration 11 nM) or [$^3$H]-5-HT (final concentration 10 nM) was added and the mixture was incubated at 37° C. for 5 minutes. After addition of 4 ml ice-cooled KRB to the assay tube, the mixture was immediately filtered through a Whatman CF/B filter under reduced pressure, and the filter was further washed with 4 ml of KRB twice. The filter was transferred to a minature vial, 4 ml of scintillator was added, and the radioactivity was counted with a liquid scintillation counter.

As a control drug, imipramine was used. The test compound was invariably tested at 4 final concentrations of $10^{-8}$, $10^{-7}$, $10^{-6}$, and $10^{-5}$M.

The data are presented in Table 17.

TABLE 17

| Example No. (Compound No.) | Monoamine uptake inhibitory activity $IC_{50}$ (µM) | |
|---|---|---|
| | NE | 5-HT |
| 2-1 | 1.04 | 0.070 |
| Imipramine | 1.12 | 0.063 |

It is apparent from Table 17 that the compound of this invention is as potent as the control drug imipramine in monoamine uptake inhibitory activity.

What is claimed is:

1. A compound of the formula

wherein Ar represents a tetracyclic fused heterocyclic group selected from the group consisting of 7-oxo-7,11b,12,13-tetrahydro-5H-isoindolo(2,1-b) (2) benzazepin-3-yl, 9-oxo-6,7,9,13b-tetrahydro-5H-isoindolo (1,2-a) (2)benzazepin-2-yl and 5-oxo-7,8,13,13a-tetrahydro-5H-isoindolo(1,2-b) (3) benzazepin-10 or 11-yl;

n represents a whole number of 1 through 10;

$R^1$ represents a hydrogen atom or a hydrocarbon group which may be substituted and may be different from one another in the repetition of n; and Y represents an unsubstituted or substituted amino or nitrogen-containing saturated heterocyclic group which may be substituted, or a salt thereof.

2. The compound according to claim 1 wherein Y is an unsubstituted or substituted piperidinyl or piperazinyl group.

3. The compound according to claim 1 which is 1-(7-oxo-7,11b,12,13-tetrahydro-5H-isoindolo[2,1-b][2]benzazepin-3-yl)-3-[4-(phenylmethyl)-1-piperazinyl]-1-propanone or a salt thereof.

4. The compound according to claim 1 which 1-(9-oxo-6,7,9,13b-tetrahydro-5H-isoindolo[1,2-a][2]benzazepin-2-yl)-3-[4-(phenylmethyl)-1-piperazinyl]-1-propanone or a salt thereof.

5. A cholinesterase inhibitory composition which contains an effective cholinesterase inhibiting amount of a compound of the formula (I) as claimed in claim 1 or a pharmaceutically acceptable salt thereof and a pharmacologically acceptable carrier.

6. A cholinesterase inhibitory composition for treating a disease caused by cholinesterase activity, which contains an effective cholinesterase inhibiting amount of a compound of the formula (I) as claimed in claim 1 or a pharmaceutically acceptable salt thereof and a pharmacologically acceptable carrier.

7. A pharmaceutical composition as claimed in claim 6 in which the disease is senile dementia and/or Alzheimer's disease.

8. A method of treating a disease caused by cholinesterase activity which comprises administering a therapeutically effective amount of a compound of the formula (I) as claimed in claim 1 or a pharmaceutically acceptable salt thereof, together with a pharmaceutically acceptable carrier to a mammal suffering from such disease.

9. A method of treating a disease as claimed in claim 8, in which the disease is senile dementia and/or Alzheimer's disease.

10. The compound according to claim 1 which is 3-(3-(1-(Phenylmethyl)-4-Piperidenyl)-1-oxopropyl)-7,11b,12,13-tetrahydro-5H-isoindolo(2,1-b)(2)benzazepin-7-one or a salt thereof.

* * * * *